US009164099B2

(12) United States Patent
Gee et al.

(10) Patent No.: US 9,164,099 B2
(45) Date of Patent: Oct. 20, 2015

(54) SITE-SPECIFIC LABELING OF AFFINITY TAGS IN FUSION PROTEINS

(71) Applicant: LIFE TECHNOLOGIES CORPORATION, Carlsbad, CA (US)

(72) Inventors: Kyle Gee, Springfield, OR (US); Aleksey Rukavishnikov, Eugene, OR (US); Courtenay Hart Kerndt, Eugene, OR (US); Richard Haugland, Olympia, WA (US); Wai-Yee Leung, San Ramon, CA (US); Wayne Patton, Newton, MA (US); Zhenjun Diwu, Okemos, MI (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 13/890,137

(22) Filed: May 8, 2013

(65) Prior Publication Data
US 2014/0038856 A1 Feb. 6, 2014

Related U.S. Application Data

(63) Continuation of application No. 13/429,972, filed on Mar. 26, 2012, now abandoned, which is a continuation of application No. 12/117,689, filed on May 8, 2008, now abandoned, which is a continuation of application No. 10/661,451, filed on Sep. 12, 2003, now abandoned.

(60) Provisional application No. 60/458,472, filed on Mar. 28, 2003, provisional application No. 60/410,612, filed on Sep. 12, 2002.

(51) Int. Cl.
*G01N 33/533* (2006.01)
*C07D 239/00* (2006.01)
*C07F 5/02* (2006.01)
*G01N 33/58* (2006.01)
*A61K 49/00* (2006.01)
*C07D 311/12* (2006.01)
*C07D 311/18* (2006.01)

(52) U.S. Cl.
CPC .......... *G01N 33/582* (2013.01); *A61K 49/0021* (2013.01); *A61K 49/0039* (2013.01); *A61K 49/0041* (2013.01); *A61K 49/0052* (2013.01); *C07D 311/12* (2013.01); *C07D 311/18* (2013.01); *C07F 5/022* (2013.01); *G01N 33/533* (2013.01)

(58) Field of Classification Search
CPC ....... G01N 33/533; G01N 33/582; C07F 5/02
See application file for complete search history.

(56) References Cited

U.S. PATENT DOCUMENTS

| 3,485,736 | A | 12/1969 | Vesterberg et al. |
| 3,980,540 | A | 9/1976 | Hoefer |
| 4,142,960 | A | 3/1979 | Hahn et al. |
| 4,337,131 | A | 6/1982 | Vesterberg |
| 4,339,327 | A | 7/1982 | Tyler |
| 4,352,751 | A | 10/1982 | Wieder et al. |
| 4,560,459 | A | 12/1985 | Hoefer |
| 4,574,040 | A | 3/1986 | Delony et al. |
| 4,603,209 | A | 7/1986 | Tsien et al. |
| 4,647,447 | A | 3/1987 | Gries |
| 4,703,004 | A | 10/1987 | Hopp |
| 4,711,955 | A | 12/1987 | Ward et al. |
| 4,774,339 | A | 9/1988 | Haugland et al. |
| 4,810,636 | A | 3/1989 | Corey et al. |
| 4,812,409 | A | 3/1989 | Babb et al. |
| 4,849,362 | A | 7/1989 | Demarinis et al. |
| 4,851,341 | A | 7/1989 | Hopp et al. |
| 4,945,171 | A | 7/1990 | Haugland et al. |
| 4,965,211 | A | 10/1990 | Wieder et al. |
| 4,978,463 | A | 12/1990 | Satoji |
| 4,978,763 | A | 12/1990 | Rocklage et al. |

(Continued)

FOREIGN PATENT DOCUMENTS

| DK | 19701382 | 7/1998 |
| JP | 08038064 | 6/1996 |

(Continued)

OTHER PUBLICATIONS

Haugland, Richard P., Handbook of fluorescent probes and research chemicals, Molecular Probes, Inc. Eugene, OR 97402-0414, USA. 1992.*
Kapanidis et al. Site-specific incorporaiton of fluorescent probes into protein: hexahistidine-tag-mediated fluorescent labeling with (Ni2+:Nitrilotriacetic acid)n-fluorochrome conjugates. J. Am. Chem. Soc. 2001, vol. 123, pp. 12123-12125.*
2003270619 Australia First Examination Report, Jun. 27, 2008.
Achour, et al., "Triethylenetetramine-N,N,N',N'',N''',N'''-hexaacetic Acid (TTHA) and TTHA-bis(butanamide) as Chelating Agents Relevant to Radio-pharmaceutical Applications", *Inorganic Chemistry*, vol. 37, 1998, 2729-2740.
Adams, et al., "New Biarsenical Ligands and Tetracysteine Motifs for Protein Labeling in Vitro and in Vivo: Synthesis and Biological Applications.", *Journal of the American Chemical Society*, vol. 124, Issue 21, May 2, 2002, 6063-6076.

(Continued)

*Primary Examiner* — Shafiqul Haq

(57) ABSTRACT

The present invention provides methods and fluorescent compounds that facilitate detecting and labeling of a fusion protein by being capable of selectively binding to an affinity tag. The fluorescent compounds have the general formula A(B)n, wherein A is a fluorophore, B is a binding domain that is a charged chemical moiety, a protein or fragment thereof and n is an integer from 1-6 with the proviso that the protein or fragment thereof not be an antibody or generated from an antibody. The present invention provides specific fluorescent compounds and methods used to detect and label fusion proteins that contain a poly-histidine affinity tag. These compounds have the general formula A(L)m(B)n wherein A is a fluorophore, L is a linker, B is an acetic acid binding domain, m is an integer from 1 to 4 and n is an integer from 1 to 6. The acetic acid groups interact directly with the positively charged histidine residues of the affinity tag to effectively label and detect a fusion protein containing such an affinity tag when present in an acidic or neutral environment.

1 Claim, 4 Drawing Sheets

(56) References Cited

U.S. PATENT DOCUMENTS

| | | |
|---|---|---|
| 5,011,912 A | 4/1991 | Hopp et al. |
| 5,047,519 A | 9/1991 | Hobbs et al. |
| 5,049,673 A | 9/1991 | Tsien et al. |
| 5,187,288 A | 2/1993 | Kang et al. |
| 5,227,487 A | 7/1993 | Haugland et al. |
| 5,238,808 A | 8/1993 | Bard et al. |
| 5,242,805 A | 9/1993 | Naleway et al. |
| 5,248,782 A | 9/1993 | Haugland et al. |
| 5,254,941 A | 10/1993 | Osika |
| 5,268,486 A | 12/1993 | Waggoner et al. |
| 5,274,113 A | 12/1993 | Kang et al. |
| 5,284,933 A | 2/1994 | Dobeli |
| 5,310,663 A | 5/1994 | Dobeli |
| 5,310,687 A | 5/1994 | Bard |
| 5,352,803 A | 10/1994 | Mattingly |
| 5,362,628 A | 11/1994 | Haugland et al. |
| 5,433,896 A | 7/1995 | Kang et al. |
| 5,442,045 A | 8/1995 | Haugland et al. |
| 5,451,343 A | 9/1995 | Neckers et al. |
| 5,453,356 A | 9/1995 | Bard |
| 5,453,517 A | 9/1995 | Kuhn et al. |
| 5,459,276 A | 10/1995 | Kuhn et al. |
| 5,478,741 A | 12/1995 | Maret et al. |
| 5,486,616 A | 1/1996 | Waggoner et al. |
| 5,501,980 A | 3/1996 | Katerinopoulos et al. |
| 5,516,911 A | 5/1996 | London et al. |
| 5,569,587 A | 10/1996 | Waggoner |
| 5,569,766 A | 10/1996 | Waggoner et al. |
| 5,573,904 A | 11/1996 | Mattingly |
| 5,578,180 A | 11/1996 | Engelhorn et al. |
| 5,585,475 A | 12/1996 | Jamieson |
| 5,616,502 A | 4/1997 | Haugland et al. |
| 5,627,027 A | 5/1997 | Waggoner |
| 5,654,176 A | 8/1997 | Smith |
| 5,696,157 A | 12/1997 | Wang et al. |
| 5,714,089 A | 2/1998 | Bard et al. |
| 5,714,327 A | 2/1998 | Houthoff et al. |
| 5,773,227 A | 6/1998 | Kuhn et al. |
| 5,798,276 A | 8/1998 | Haugland et al. |
| 5,804,400 A | 9/1998 | Martin et al. |
| 5,830,912 A | 11/1998 | Gee et al. |
| 5,846,737 A | 12/1998 | Kang |
| 5,847,162 A | 12/1998 | Lee et al. |
| 5,863,753 A | 1/1999 | Haugland et al. |
| 5,869,689 A | 2/1999 | Zhang et al. |
| 5,922,185 A | 7/1999 | Updyke et al. |
| 6,013,462 A | 1/2000 | Kauvar |
| 6,017,712 A | 1/2000 | Lee et al. |
| 6,025,505 A | 2/2000 | Lee et al. |
| 6,048,982 A | 4/2000 | Waggoner et al. |
| 6,057,106 A | 5/2000 | Updyke |
| 6,059,948 A | 5/2000 | Updyke et al. |
| 6,080,852 A | 6/2000 | Lee et al. |
| 6,096,182 A | 8/2000 | Updyke et al. |
| 6,113,766 A | 9/2000 | Steiner et al. |
| 6,117,976 A | 9/2000 | Neri et al. |
| 6,130,101 A | 10/2000 | Mao et al. |
| 6,140,138 A | 10/2000 | Bard |
| 6,143,154 A | 11/2000 | Updyke et al. |
| 6,156,182 A | 12/2000 | Olech et al. |
| 6,162,338 A | 12/2000 | Updyke et al. |
| 6,162,931 A | 12/2000 | Gee et al. |
| 6,270,969 B1 | 8/2001 | Hartley et al. |
| 6,303,128 B1 | 10/2001 | Webb |
| 6,316,276 B1 | 11/2001 | Gregory et al. |
| 6,316,409 B1 | 11/2001 | Neri |
| 6,339,392 B1 | 1/2002 | Ashihara et al. |
| 6,348,559 B1 | 2/2002 | Fujimori et al. |
| 6,399,392 B1 | 6/2002 | Haugland et al. |
| 6,403,807 B1 | 6/2002 | Singh et al. |
| 6,495,017 B1 | 12/2002 | Islam et al. |
| 6,562,213 B1 | 5/2003 | Cabilly et al. |
| 6,562,632 B1 | 5/2003 | Szalecki et al. |
| 6,564,176 B2 | 5/2003 | Kadtke |
| 6,579,718 B1 | 6/2003 | Yue et al. |
| 6,599,410 B1 | 7/2003 | Steiner et al. |
| 6,623,655 B1 | 9/2003 | Kappel et al. |
| 6,664,047 B1 | 12/2003 | Haugland et al. |
| 6,670,194 B1 | 12/2003 | Aebersold et al. |
| 6,716,979 B2 | 4/2004 | Diwu et al. |
| 6,872,574 B2 | 3/2005 | Cravatt et al. |
| 6,919,333 B2 | 7/2005 | Ebright et al. |
| 6,974,873 B2 | 12/2005 | Leung et al. |
| 6,977,305 B2 | 12/2005 | Leung et al. |
| 7,033,520 B2 | 4/2006 | Kappel et al. |
| 2002/0134680 A1 | 9/2002 | Cabilly |
| 2003/0040016 A1 | 2/2003 | Singh et al. |
| 2003/0077616 A1 | 4/2003 | Lomas |
| 2004/0038306 A1* | 2/2004 | Agnew et al. ............ 435/7.1 |
| 2004/0146950 A1 | 7/2004 | Howe |
| 2004/0171034 A1 | 9/2004 | Agnew et al. |
| 2009/0004641 A1 | 1/2009 | Gee et al. |
| 2009/0081722 A1 | 3/2009 | Gee et al. |

FOREIGN PATENT DOCUMENTS

| | | |
|---|---|---|
| WO | 94/18986 | 9/1994 |
| WO | 95/27197 | 10/1995 |
| WO | 98/57161 | 12/1998 |
| WO | 99/37813 | 7/1999 |
| WO | 02/09220 | 1/2002 |
| WO | 02/12195 | 2/2002 |
| WO | 02/18901 | 3/2002 |
| WO | 02/071024 | 9/2002 |
| WO | 03/015426 | 2/2003 |

OTHER PUBLICATIONS

Amano, et al., "A new fluorescent reagent for the detection of proteins having histidine-tag (his-tag).", *Analytical Sciences* vol. 17, 2001, pp. 1469-1471.

Berge, S. et al., "Pharmaceutical Salts", *Journal of Pharmaceutical Science*, vol. 66, 1977, 1-19.

Borjigin, J., "Insertional Mutagenesis as a Probe of Rhodospin's Topography, Stability, and Activity", *Proceedings of the National Academy of Sciences (PNAS)*, 269, No. 20, 1994, 14715-14722.

Botting, C. et al., "System for Recombinant Proteins", *BioTechniques* vol. 19, Reporter Enzyme-Nitrilotriacetic Acid-Nickel Conjugates: Reagents for Detecting Histidine-Tagged Proteins, 1995, 362-363.

Bouizar, Z. et al., "Purification and Characterization of Calcitonin Receptors in Rat Kidney Membranes by Covalent Cross-Linking Techniques.", *Eur. J. Biochem*, vol. 155, No. 1, 1986, pp. 141-147.

Briand, J., et al., "Synthetic Peptides as Antigens: Pitfalls of Conjugation Methods", *Journal of Immunological Methods*, vol. 78, No. 1, Apr. 8, 1985, 59-69.

Brizzard, et al., "Immunoaffinity Purification of FLAG.RTM. Epitope-Tagged Bacterial Alkaline Phosphatase Using a Novel Monoclonal Antibody and Peptide Elution", *BioTechniques*, 16, 1994, 730-734.

Browning, et al., "Studies on the Differing Effects of the Tumor Necrosis Factor and Lymphotoxin on the Growth of Several Human Tumor Lines", *Journal of Immunology*, vol. 143, Issue 6, 1989, pp. 1859-1867.

Buranda, T et al., "Real Time Detection of Epitope-Tagged Proteins in Flow Cytometry: FRET Based Assays on Beads with Sub-Femtomole Resolution.", *Analytical Biochemistry*, 298, 2001, 151-162.

Camera, E. et al., "Analytical Methods to Investigate Glutathione and Related Compounds in Biological and Pathological Processes (Review)", *Journal of Chromatography B*, vol. 781, 2002, 181-206.

Chahboun, J. et al., "Are histidine rings the main potential sites of the interaction between proteins and the fluorescent Mg-2+ indicator Mag-indol?", *Journal of Photochemistry and Photobiology and B Biology* vol. 33(2), 1996, 125-130.

Chiou, et al., "Evaluation of Commonly Used Electrophoretic Methods for the Analysis of Proteins and Peptides and their Application of Biotechnology", *Analytica Chimica Acta*, Ch. 383, 1999, 47-60.

Corson, D. et al., "Efficient Multigram Synthesis of the Bifunctional Chelating Agent (S)-1-p-isothiocyanatobenzyl-

(56) References Cited

OTHER PUBLICATIONS diethylenetriaminepentaacetic acid [Correction of Diethylenetetraminepentaacetic Acid].", *Bioconjugate Chem.*, vol. 11, No. 2, 2000, 292-299.

Crowe, et al., "Methods in Molecular Biology", *Harwood, A. J., eds., Humana Press, Inc.* Otawa, 31(35), 1994, 371-387.

Dent, et al., "Regulation of raf-1 and raf-1 mutants by ras-dependent and ras-independent mechanisms in vitro.", *Mol. Cell Biol.*, 15, 1995, 4125-4135.

Di Paolo, G et al., "Targeting of SCG10 to the Area of the Golgi Complex Is Mediated by Its NH2-terminal Region", *The Journal of Biological Chemistry*, vol. 272, 1997, 5175-5182.

Dolnik, Vladislav , "Capillary zone electrophoresis of proteins", *Electrophoresis*, vol. 18, 1997, 2353-2361.

Drevin, Haakan , "Covalent Coupling of Proteins to Erythrocytes by Isocyanide. A New, Sensitive and Mild Technique for Identification and Estimation of Antibodies by Passive Hemagglutination", *Journal of Immunological Methods*, vol. 77, No. 1, Feb. 28, 1985, 9-14.

Einhauer, A. et al., "The FLAG peptide, a versatile fusion tag for purification of recombinant proteins.", *J. Biochem Biophys Methods*, vol. 49, 2001, 455-465.

Evan, G. L. et al., "Isolation of monoclonal antibodies specific for human c-myc proto-oncogene product", *Mol. Cell Biol.*, 5, 1985, 3610-3616.

Fanou-Ayi, L et al., "Metal-chelate Affinity Chromatography as a Separation tool", *Annals new York Academy of Sciences*, vol. 413, 1983, 300-306.

Farinas, et al., "Receptor-mediated targeting of fluorescent probes in living cells", *J. Biol. Chem.* vol. 274, No. 12,, 1999, pp. 7603-7606.

Field, J et al., "Purification of a RAS-responsive adenylyl cyclase complex from *Saccharomyces cerevisiae* by use of an epitope addition method", *Mol. Cell. Biol.*, 8, 1988, 2159-2165.

Fischer, C. et al., "Cloning and characterization of the *Bacillus subtilis* prkA gene encoding a novel serine protein kinase", *Gene*, 168, 1996, 55-60.

Furniss, B. et al., "Resolution of Racemates", *Vogel's Textbook of Practical Organic Chemistry*, Fifth Ed, Longman Group UK Ltd., Essex, 1989, 809-823.

Gerard, N. et al., "Construction and expression of a novel recombinant anaphylatoxin, C5a-N19, as a probe for the human C5a receptor", *Biochemistry*, vol. 29, No. 39, 1990, 9274-9281.

Goldstein, D. J. et al., "The BPV-1 E5 Oncoprotein Expressed in Schizosaccharomyces Pombe Exhibits Normal Biochemical Proteins and Binds to the Endogenous 16-kDa Component of the Vacuolar Proton-ATPase", *Virology*, 190, 1992, 889-893.

Griffin, B. et al., "Fluorescent labeling of Recombinant Proteins in Living Cells with Flash", *Methods in Enzymology*, vol. 327,, 2000, 565-578.

Griffin, B. et al., "Specific Covalent Labeling of Recombinant Protein Molecules Inside Live Cells", *Science*, vol. 281, Issue 5374,, Jul. 10, 1998, 269-272.

Grussenmeyer, T. et al., "Complexes of Polyoma Virus Medium T Antigen and Cellular Proteins", *Biochemistry*, 82, 1985, 7952-7954.

Guttman, A. et al., "Analytical and Micropreparative Ultrahigh Resolution of Oligonucleotides by Polyacrylamide Gel High-Performance Capillary Electrophoresis", *Anal. Chem.*, vol. 62, 1990, 137-141.

Hainfeld, J. et al., "Ni-NTA-Gold Clusters Target His-Tagged Proteins", *J. Struct. Biol.*, 127, 1999, 195-198.

Hart, C. et al., "Fluorescene detection and quantitation of recombinant proteins containing oligohistidine-tag sequences directly in SDS-polyacrylamide gels", *Molecular Probes, Inc*, Mar. 2002, 1-10.

Heller, A. , "Electrical Wiring of Redox Enzymes", *Acc. Chem. Res.*, vol. 23, No. 5, 1990, 128-134.

Hentz, N. et al., "Affinity chromatography of recombinant peptides/proteins based on a calmodulin fusion tail.", *Anal Chem*, 68, 1996, 1550-5.

Hjerten, S. , "High-Performance Electrophoresis: the Electrophoretic Counterpart of High-Performance Liquid Chromatography", *Journal of Chromatography*, vol. 270, 1983, 1-6.

Hochuli, E et al., "New Metal Chelate Absorbent Selective for Proteins and Peptides containing Neighboring Histidine Residues", *J. Chromatography*, 411, 1987, 177-184.

Hochuli, Erich, "Interaction of Hexahistidine Fusion Proteins with Nitrilotriacetic Acid-Chelated Ni2+ Ions", *Methods: A Companion to Methods in Enzymology*, vol. 4, 1992, 68-72.

Hopp, Thomas P. et al., "A Short Polypeptide Marker Sequence Useful for Recombinant Protein Identification and Purification", *Biotechnology*, vol. 6, Oct. 1988, 1204-1210.

Hubert, et al., "Metal Chelate Affinity Chromatography", *Journal of Chromatography*, vol. 198, 1980, 247-255.

Jacob, F. et al., "Deletions fusionnant l'operon lactose et un operon purine chez *Escherichia coli*.", *J. Mol. Biol*, vol. 31, Jun. 8, 1965, 704-719.

Jin, L. et al., "Use of Alfa-N, N-Bis [Carboxymethyl] lysine-Modified Peroxidase in Immunoassays", *Analytical Biochemistry*, vol. 229, 1995, 54-60.

Jung, S.. et al., "Crosslinking of platelet glycoprotein lb by N-succinimidyl(4-azidophenyldithio)propionate and 3,3'-dithiobis-(sulfosuccinimidyl propionate)", *Biochimica et Biophysica Acta*, vol. 761, Iss. 2, 1983, pp. 152-162.

Kapanidis, A.. et al., "Site-specific incorporation of fluorescent probes into protein: hexahistidine-tag-mediated fluorescent labeling with (Ni(2+) : Nitrilotriacetric Acid (n)-fluorochrome conjugates", *Journal of the American Chemical Society*, vol. 123, No. 48, Dec. 5, 2001, 12123-12125.

Kaplan, W. et al., "Conformational stability of pGEX-expressed *Schistosoma japonicum* glutathione S-transferase: a detoxification enzyme and fusion-protein affinity tag.", *Protein Science*, vol. 6, 1997, 399-406.

Kato, et al., "Construction of a human full-length cDNA bank", *Gene*, vol. 150, No. 2, Dec. 15, 1994, 243-250.

Kitagawa, et al., "Enzyme Coupled Immunoassay of Insulin Using a Novel coupling reagent", *J Biochem* (Tokyo), vol. 79 No. 1, 1976, 233-236.

Koralnik, L. et al., "The p12I, p13II, and p30II proteins encoded by human T-cell leukemia/lymphotropic virus type I open reading frames I and II are localized in three different cellular compartments.",*J. Virol*, 67, 1993, 2360-2366.

Kreis, T. , "Microinjected antibodies against the cytoplasmic domain of vesicular stomatitis virus glycoprotein block its transport to the cell surface.", *EMBO Journal*, vol. 5 No. 5, 1986, 931-941.

Lee, J.. et al., "A Protein Kinase Involved in the Regulation of Inflammatory Cytokine Biosynthesis", *Nature*, vol. 372, No. 22, Dec. 29, 1994, 739-746.

Lew, A. et al., "Recombinant Fusion Proteins of Protein A and Protein G with Glutithione S-Transferase as Reporter Molecules", *Journal of Immunological Methods*, vol. 136, No. 2, Feb. 15, 1991, 211-219.

Liang, T.,. et al., "Antibody Binding to a Peptide but Not the Whole Protein by Recognition of the C-Terminal Carboxy Group", *Arch. Biochem. Biophys.*, 329, 1996, 208-214.

Lim, P., et al., "Distribution and specific identification of papillomavirus major capsid protein epitopes by immunocytochemistry and epitope scanning of synthetic peptides.", *J. Infect. Dis.*, 162, 1990, 1263-1269.

Lindner, P et al., "Specific Detection of His-Tagged Proteins With Recombinant Anti-his Tag scFv-Phosphatase or scFv-Phage Fusions", *Biotechniques*, vol. 22 No. 1, Jan. 1997, 140-149.

Lopez, M.. , "Advantages of carrier Ampholyte IEF", *Methods Molecular Biology*, vol. 112, 2-D Proteome Analysis Protocols, 1999, 109-110.

Luo, W. et al., "A universal tag for recombinant proteins.", *Archives of Biochemistry and Biophysics*, vol. 329, No. 2, Article# 0211, May 15, 1996, 215-220.

MacArthur, et al., "Monoclonal antibodies specific for the carboxy terminus of simian virus 40 large T antigen.", *J. Virol*, 52, 1984, 483-491.

Majima, E. et al., "Stabilities of the Fluorescent SH-Reagent Eosin-5-Maleimide and its Adducts with Sulfhydryl Compounds", *Biochemica et Biophysica Acta*, vol. 1243, 1995, 336-342.

Malone, J. et al., "Practical aspects of fluorescent staining for proteomic applications.", *Electrophoresis*, vol. 22 No. 5, 2001, 919-32.

(56) References Cited

OTHER PUBLICATIONS

Maniatis, et al., "Molecular Cloning", *Cold spring Harbor Laboratory*, 1982, 468-469.
Martin, G. et al., "The GAP-Related Domain of the Neurofibromatosis Type 1 Gene Product Interacts with ras p21", *Cell*, 63, 1990, 843-849.
Matsui, N. et al., "Ch 23: Running preparative carrier ampholyte and immobilized pH gradient IEF gels for 2-D", *2-D Proteome Analysis Protocols*, vol. 112, Methods in Molecular Biology, 1999, 211-219.
McMahan, S. et al., "Single-step synthesis and characterization of biotinylated nitrilotriacetic acid, a unique reagent for the detection of histidine-tagged proteins immobilized on nitrocellulose.", *Analytical Biochemistry*, vol. 236, 1996, 101-106.
Molecular Probe, "Handbook of Fluorescent probes and research products, Molecular Probes Inc.", 2001, 1-7 pgs.
Mosbach, K. et al., "Formation of Proinsulin by Immobilized *Bacillus subtilis*", *Nature*, 302, 1983, 543-545.
Munro, S. et al., "A C-Terminal Signal Prevents Secretion of Luminal ER Proteins", *Cell*, 48, 1987, 899-907.
Nock, S., "Reversible, site-specific immobilization of polyarginine-tagged fusio proteins on mica surfaces", *FEBS Letters*, vol. 414, 1997, 233-238.
O'Farrell, P. et al., "High Resolution Two-Dimensional Electrophoresis of Proteins", *Journal of Biological Chemistry*, vol. 250, No. 10, May 25, 1975, 4007-4021.
O'Shannessy, D. et al., "Detection and Quantitation of Hexa-Histidine-Tagged Recombinant Proteins on Western Blots and by a Surface Plasmon Resonance Biosensor Technique", *Analytical Biochemistry*, vol. 229, No. 1, 1995, 119-124.
Palva, L. et al., "Secretion of interferon by *Bacillus subtilis*.", *Gene*. 22, 1983, 229-235.
Park, L. et al., "Characterization of the Cell Surface Receptor for a Multi-Lineage Colony-Stimulating Factor (CSF-2alpha)", *J. Biol. Chem.*, vol. 261, No. 1, 1986, 205-210.
PCT/US03/28738 International Search Report, Jan. 28, 2005.
PCT/US2004/034460 International Preliminary Report on Patentability, Issued, Apr. 18, 2006, pp. 1-10.
PCT/US2004/034460 International Search Report, Oct. 20, 2005.
PCT/US2004/034460 Written Opinion, Oct. 20, 2005.
Pogge Von Strandmann, et al., "A highly specific and sensitive monoclonal antibody detecting histidine-tagged recombinant proteins", *Protein Eng.*, vol. 8, No. 7, 1995, 733-735.
Von Strandmann, P., et al. "A highly specific and sensitive monoclonal antibody detecting histidine-tagged recombinant proteins", *Protein Eng.* vol. 8, No. 7 1995, 733-735.
Porath, J et al., "Immobilized metal ion affinity chromatography", *Protein Expr Purif*, vol. 3 No. 4, 1992, 263-281.
Porath, J. et al., "Metal chelate affinity chromatography, a new approach to protein fractionation", *Nature*, 258, 1975, 598-599.
Prickett, K. S. et al., "A Calcium-Dependent Antibody for Identification and Purification of Recombinant Proteins", *BioTechniques*, 7, 1989, 580-589.
Rabilloud, Thierry et al., "Ruthenium II tris (bathophenathroline disulfonate) a powerful fluorescent stain for detection of proteins in gel with minimal interference in subsequent mass spectrometry analysis", *Springer-Verlag 2000*, 2000, 1-14 pages.
Righetti, Pier G. et al., "Immobilized Buffers for Isoelectric Focusing: From Gradient Gels to Membranes", *Electrophoresis*, vol. 15, 1994, 1040-1043.
Righetti, Pier G. et al., "Isoelectric Focusing in Immobilized pH Gradients", *Methods in Enzymology*, vol. 270, 1996, 235-255.
Righetti, Pier G. et al., "Oxidation of alkaline immobiline buffers for isoelectric focusing in immobilized pH gradients", *Applied and Theoretical Electrophoresis*, vol. 1, 1989, 99-102, 103-107.

Ritchie, et al., "Baculovirus expression and biochemical characterization of the human microsomal triglyceride transfer protein.", *Biochem Journal*, 338, 1999, 305-10.
Roth, et al., "A Conserved Family of Nuclear Phosphoproteins Localized to Sites of Polymerase II Transcription", *J. Cell Biol*, 115, 1991, 587-596.
Rubinfeld, B. et al., "Molecular cloning of a GTPase activating protein specific for the Krev-1 protein p21rap1.", *Cell*, 63, 1991, 1033-1042.
Sandler, Stanley R. et al., "Organic Functional Group Preparations", vol. 3, *New York: Academic Press*, 1972, 5-9.
Shen, et al., "Hydrazide as a ligand moiety in immobilized metal ion affinity chromatography. Separation of BO-IMA and BODIPYhydrazide", *Journal of Chromatography*, 1997, pp. 261-265.
Smith, D. J., "Mini-Exon Epitope Tagging for Analysis of the Protein Coding Potential of Genomic Sequence", *BioTechniques*, 23, 1997, 116-120.
Stora, T. et al., "Metal ion trace detection by a Chelator-Modified gold electrode: A comparison of surface to Bulk affinity", *Langmuir*, vol. 13, No. 20, Oct. 1, 1997, pp. 5212-5214.
Ternynck, T. et al., "Conjugation of p-Benzoquinone Treated Enzymes with Antibodies and Fab Fragments", *Immunochemistry*, vol. 14, 1977, 767-774.
Terpe, K , "Overview of tag protein fusions: from molecular and biochemical fundamentals to commercial systems.", *Applied Microbiology and Biotechnology*, vol. 60, Jan. 2003, 523-533.
Turner, Jerrold R. et al., "Carboxyl-terminal Vesicular Stomatitis Virus G Protein-tagged Intestinal Na-dependent Glucose Cotransporter (SGLT1)", *American Society for Biochemistry and Molecular Biology*, vol. 271, No. 13, Mar. 29, 1996, 7738-7744.
Wilson, I. A. et al., "The Structure of an Antigenic Determinant in a Protein", *Cell*; vol. 37, 1984, 767-778.
Winzerling, J. et al., "How to Use Imobilized Metal Ion Affinity Chromatography", *Methods: A Companion to Methods in Enzymology*, vol. 4, 1992, 4-13.
Wong, Shan H. , "Chemistry of Protein Conjugation and Cross-linking", *CRC Press*, Boca Raton, FL, 1991.
Wouters, F. S. et al., "Imaging Protein—Protein Interactions by Florescence resonance Energy Transfer (FRET) Microscopy", *Current Protocols in Protein Science; Unit 19.5*, 2001, 19.5.1-19.5.15.
Xanthene and Xanthene Dye, , *Hawley's Condensed Chemical Dictionary*, 14d., John Wiley and Sons, Inc., 2002.
Xu, T. et al., "Analysis of genetic mosaics in developing and adult *Drosophila* tissues.", *Development*, vol. 117, No. 4, 1993, 1223-1237.
Xu, Y. et al., "E1A-Mediated Repression of Progesterone Receptor-Dependent Transactivation Involves Inhibition of the Assembly of a Multisubunit Coactivation Complex", *Mol. Cell Biol.*, 20, 2000, 2138-2146.
Yip, T et al., "Immobilized metal ion affinity chromatography", *Molecular biotechnol.*, 1, 1994, 151-164.
Zarling, David A. et al., "Mapping of Lymphocyte Surface Polypeptide Antigens by Chemical Cross-Linking with BSOCOES", *Journal of Immunology*, vol. 124, No. 2, 1980, 913-920.
Zentgraf, Hanswalter et al., "Detection of histidine-tagged fusion proteins by using a high-specific mouse monoclonal anti-histidine tag antibody", *Nucleic Acids Research*, vol. 23, No. 16, 1995, 3347-3348.
EP 03752325; Supplementary European Search Report mailed Jan. 9, 2007; 3 pages.
Chiang, et al., "Satellite hole spectral method and its applications to dye-DNA complexes", *Proc. Natl. Sci. Counc. ROC(A)*, vol. 23, No. 6, 1999; pp. 679-694.

\* cited by examiner

US 9,164,099 B2

SITE-SPECIFIC LABELING OF AFFINITY TAGS IN FUSION PROTEINS

CROSS-REFERENCE TO RELATED APPLICATIONS

This is a continuation application and claims the benefit of U.S. application Ser. No. 13/429,972 filed Mar. 26, 2012, which is a continuation application and claims the benefit of U.S. application Ser. No. 12/117,689, filed May 8, 2008, now abandoned, which claims the benefit of U.S. application Ser. No. 10/661,451, filed Sep. 12, 2003, now abandoned, which claims the benefit of U.S. Provisional Application No. 60/458,472 filed Mar. 28, 2003, and U.S. Provisional Application No. 60/410,612, filed Sep. 12, 2002, all of which are commonly owned with this application and the disclosures of which are hereby expressly incorporated by reference in their entirety as though fully set forth herein.

INTRODUCTION

1. Field of the Invention

The present invention relates to novel compositions and methods for the detection and isolation of fusion proteins comprising affinity tag sequences. The invention has applications in the fields of molecular biology and proteomics.

2. Background of the Invention

The present invention relates to fluorescent compounds that have selective affinity, and bind with specificity to affinity tag-containing fusion proteins. Such compounds being particularly useful for the detection, site-specifically labeling and monitoring of desired recombinant fusion proteins.

Typically, recombinant fusion proteins comprise a synthetic leader peptide or protein fragment linked to independently derived polypeptides. In 1965 it was demonstrated that an amino acid sequence not normally part of a given operon can be inserted within the operon and be controlled by the operon (Jacob, F. et al. (1965) J. Mol. Biol. 13, 704). Therefore, the leader sequence of recombinant fusion proteins can facilitate protein expression, detection and purification by providing, for example, enzymatic activity enabling identification of fusion proteins, an amino acid sequence recognized by cellular secretory mechanism, or a sequence having distinctive chemical or antigenic characteristics useful in purifying and detection of the fusion protein by ion exchange, reverse phase, immunoaffinity and affinity chromatographic media. In general, polyanionic peptides and polycationic peptides bind to ion-exchangers, hydrophobic peptides bind to reverse-phase media and peptides that are immunogenic can be bound by antibodies.

Immobilized metal-ion affinity chromatography (IMAC) relies upon the interaction of exposed histidine and cysteine residues on proteins with certain transition metals, such as $Ni^{2+}$, $Co^{2+}$, $Zn^{2+}$, $Cu^{2+}$ and $Fe^{3+}$ (Porath, J., et al. (1975) Nature 258:598-599; Winzerling, J., et al. (1992) Methods 4:4-13; Yip, T. and Hutchens, T. (1994) Molecular Biotechnol. 1:151-164). Protein interaction with immobilized metal ions is a selective and versatile, high-affinity adsorption procedure. The basic principles of IMAC are commonly exploited to facilitate the purification of recombinant proteins.

The poly-histidine affinity tag is a transition metal-binding peptide sequence comprising a string of four to ten histidine residues. When a DNA sequence corresponding to the poly-histidine affinity tag is fused in frame with a gene, the resulting fusion protein can readily be purified by IMAC using a nickel- or cobalt-charged resin. Though a variety of fusion affinity tags have been developed over the years, the poly-histidine affinity tag is popular because it requires minimal addition of extra amino acids to the recombinant protein, rarely interferes with protein folding, is poorly immunogenic and allows for rapid purification of the target protein by IMAC.

Unfortunately, the detection of poly-histidine affinity tag containing fusion proteins after electrophoresis usually requires multiple time-consuming steps, including transfer of the gel to a membrane, blocking of unoccupied sites on the membrane with protein or detergent solutions, incubation with a poly-histidine affinity tag-binding agent (primary antibody, biotin-nitrilotriacetic acid or HRP-nitrilotriacetic acid), incubation with a secondary detection agent (antibody-reporter enzyme conjugate, streptavidin-reporter enzyme conjugate), and incubation with a visualization reagent (colorimetric, fluorogenic or chemiluminescent reagent). Specifically, biotinylated nitrilotriacetic acid (NTA) has been used in combination with streptavidin-horseradish peroxidase or streptavidin-alkaline phosphatase conjugates and chemiluminescent or colorimetric substrates in order to detect poly-histidine affinity tag containing fusion proteins after electroblotting (Hochuli, E. and Piesecki, S. (1992) Methods 4: 68-72; O'Shannessy, D., et al. (1995) Anal. Biochem. 229:119-124; McMahan, S. and Burgess, R. (1996) Anal Biochem. 236: 101-106). In addition, direct reporter enzyme-nitrilotriacetate-nickel conjugates have been employed for detection of poly-histidine affinity tag containing fusion proteins on electroblots (Botting, C. and Randall, R. (1995) BioTechniques 19: 362-363; Jin, L., et al. (1995) Anal. Biochem. 229: 54-60). Similarly, colloidal gold with nitrilotriacetic acid conjugated to its surface has been employed to detect poly-histidine affinity tag containing fusion proteins on blots after a silver enhancement step (Hainfeld, J., et al. (1999) J. Struct. Biol. 127: 185-198). Finally, though poly-histidine affinity tag is not particularly immunogenic, a number of high affinity monoclonal antibodies specific to the peptide have been generated to detect affinity tag containing fusion proteins by standard electroblotting methods (Zentgraf, H., et al. (1995) Nucleic Acids Res. 23: 3347-3348; Pogge von Strandmann, E., et al. (1995) Protein Eng. 8: 733-735; Lindner, P., et al. (1997) BioTechniques 22: 140-149).

Examples of immunogenic affinity tags include protein A, c-myc (Roth et al, (1991) J. Cell Biol.115:587-596), myc (EQKLISEEDL; Evan G I, et al. (1985) Mol. Cell Biol. 5:3610-3616; Munro S. and Pelham H R B, (1987) Cell 48:899-907; Borjigin J. and Nathans J., (1994) 269:14715-14727; Smith D J, (1997) BioTechniques 23:116-120) FLAG® (Hopp T. P. et al. (1988) Biotechnology 6:1204; Prickett, K. S. et al. (1989) BioTechniques 7:580-589; Gerard N P and Gerard C, (1990) Biochemistry 29:9274-9281; Einhauer A. and Jungbauer A. (2001) J. Biochem Biophys. Methods 49:455-465; U.S. Pat. Nos. 4,703,004; 4,851,341 and 5,011,912), GST (Glutathione-S-transferase), HA, derived from the influenza hemagglutinin protein (Wilson I A, et al., (1984) Cell, 37:767; Field J. et al. Mol. Cell Biol. (1988) 8:2159-2165; Xu Y, et al. (2000) Mol Cell Biol. 20:2138-2146), IRS (RYIRS; Liang T C et al. (1996) 329:208-214; Luo W et al (1996) Arch. Biochem. Biophys. 329:215-220), AU1 and AU5 (DTYRYI and TDFLYK; Lim P S et al. (1990) J. Infect. Dis. 162:1263-1269; Goldstein D J et al. (1992) 190:889-893; Koralnik I J et al. (1993) J. Virol. 67:2360-2366), glu-glu (a 9 amino acid epitope from polyoma virus medium T antigen, EEEEYMPME; Grussenmeyer, T. et al. (1985) PNAS. USA 82:7952-7954; Rubinfeld. B. et al. (1991) Cell 65:1033-1042), KT3 (an 11 amino acid epitope from the SV40 large T antigen, KPPTPPPEPET; MacArthur H. and Walter G. (1984) J, Virol. 52:483-491; Martin G A et al. (1990) 63:843-849; Di Paolo G et al. (1997) 272:5175-5182), T7 (an 11 amino acid leader peptide from T7 major capsid protein), S-TAG, HSV (an 11 amino acid peptide from herpes simplex virus glycoprotein D), VSV-G (an 11 amino acid epitope from the carboxy terminus of vesicular stomatitis virus glycoprotein, YTDIEMNRLGK; Kreis T. (1986) EMBO J. 5:931-941; Turner J R et al (1996) 271:7738-7744), Anti-Xpress (8 amino acid epitope, DLYDDDK), and VS (14 amino acid epitope from paramoxyvirus SV5, GKPIPNPLLGLDST).

Typically, immunogenic affinity tags are detected with labeled antibodies wherein the label can be an enzyme, fluorophore, hapten or any label known to one skilled in the art and the antibodies, directly or indirectly, detect the affinity containing fusion protein. Immunogenic affinity tags can also be detected in a multistep assay using ruthenium labeled anti-affinity tag antibodies that produce electrochemiluminescence (ECL) (ORIGEN®, U.S. Pat. Nos. 5,310,687; 5,714,089; 5,453,356; 6,140,138; 5,804,400 and 5,238,808) indicating the presence of the affinity tag. Electrochemiluminescence is the process by which light generation occurs when a low voltage is applied to an electrode, triggering a cyclical oxidation and reduction reaction of a ruthenium metal ion bound to the compound to be detected. The ruthenium labeled antibody is captured on a solid surface by the affinity tag, a second oxidation reaction component, tripropylamine (TPA), is introduced into the cell and a voltage is applied. The TPA reduces the ruthenium, which receives the electron in an excited state and then decays to the ground state releasing a photon in the process.

The FLAG® affinity tag was designed in conjunction with antibodies for the purpose of detection and purification of fusion proteins (Hopp T. P. et al. (1988) Biotechnology 6:1204; Prickett, K. S. et al. (1989) BioTechniques 7:580-589, supra). As such, the use of anti-FLAG® antibodies are widely used to detect and purify FLAG® affinity tag containing fusion proteins. The FLAG® sequence typically consists of DYKDDDDK, D=Asp, Y=Tyr and K=Lys, but any combination of 3 to 6 aspartic or glutamic acid residues is also considered a FLAG® sequence. The sequence is hydrophilic and highly immunogenic. The FLAG® affinity tag has effectively been used in various expression systems for the detection and purification of recombinant fusion proteins (Brizzard et al. (1994) BioTechniques 16:730-735; Lee et al. (1994) Nature 372:739-746; Xu et al. (1993) Development 117:1223-1237; Dent et al. (1995) Mol. Cell Biol. 15:4125-4135; Ritchie et al. (1999) BioChem Journal 338:305-10.) Recently, the FLAG® affinity tag was used to detect fusion proteins wherein the use of antibodies was not employed (Buranda T. et al. (2001) Anal. Biochemistry 298:151-162). The FLAG® sequence was synthesized with fluorescein and/or biotin as a label and tag, respectively, wherein the peptides were bound to streptavidin beads and the fluorescein was detected using flow cytometry.

While antibodies against GST are available for both purification and detection (Molecular Probes, Inc., Eugene, Oreg.) the affinity tag is typically purified using glutathione resin (U.S. Pat. Nos. 5,654,176; 6,303,128 and 6,013,462). Glutathione is a ubiquitous tripeptide that binds with high affinity to the GST enzyme.

An affinity tag that is not generally immunogenic and does not readily bind metal ions or chemical moieties includes calmodulin-binding peptides (U.S. Pat. Nos. 5,585,475; 6,316,409 and 6,117,976). These affinity tags are routinely purified using columns wherein beads are covalently attached to calmodulin. In the presence of calcium the calmodulin protein binds the calmodulin affinity tag with high affinity because calcium induces a conformational change in calmodulin increasing the affinity of the protein for the affinity tag. Calmodulin affinity tags are advantageous in certain applications because the captured fusion protein can be eluted from a column using a metal chelating moiety instead of harsh denaturing conditions.

Another affinity tag that is not generally immunogenic includes the binding site for the FlAsH reagent, CCXXCC wherein X is an amino acid other than cysteine (Griffin et al (2000) Methods in Enzymology 327:565-578; Griffin et al (1998) Science 281:269-272; Thorn et al (2000) Protein Science 9:213-217). The FlAsH reagent is a fluorescein molecule that has been substituted by two arsenical groups such that the reagent interacts with the α-helical structure of the CCXXCC sequence (Adams et al (2002) Journal of American Chemical Society 124: 6063-6076). For binding to occur the thiols of the cysteine residues must not be disulfide bonded or chelated by a metal ion. Thus, the FlAsH reagent is typically used to label proteins in vivo due to these limitations for in vitro labeling. Therefore a reducing agent must be used for binding to occur and a buffer must be free of metal ions.

The fluorescent compounds and methods of the present invention have been developed for the fluorescence detection of affinity tag containing fusion proteins directly in polymeric gels (with or without sodium dodecyl sulfate (SDS)), without the requirement for electroblotting, blocking, reporter enzymes or secondary detection reagents. These present fluorescent compounds are advantages over FlAsH wherein a reducing agent is not required and a metal ion may be present in the buffer solution. These compounds take advantage of the charged residues of the affinity tag wherein the binding domains of the present invention are covalently attached to a fluorophore for selective detection of a wide range of affinity tag containing fusion proteins. These compounds and methods of the present invention provide a significant improvement over the prior art for detecting, monitoring and quantitating affinity tag containing fusion proteins.

SUMMARY OF THE INVENTION

The present invention provides methods and fluorescent compounds that specifically and selectively bind to affinity tags of fusion proteins. The compounds of the present invention facilitate detecting and labeling of a fusion protein by being capable of selectively binding to an affinity tag. The methods for detecting a fusion protein containing an affinity tag comprises contacting a sample with a staining solution and then illuminating the sample whereby the fusion protein is detected. The staining solution comprises a fluorescent compound and a buffer wherein the buffer optionally comprises a metal ion. The fluorescent compounds, as used herein, are defined as a compound that is capable of selectively binding, directly or indirectly to an affinity tag.

The fluorescent compounds have the general formula A(B)n, wherein A is a fluorophore, B is a binding domain that is a charged chemical moiety, a protein or fragment thereof and n is an integer from 1-6 with the proviso that the protein or fragment thereof not be an antibody or generated from an antibody. The binding domain of the fluorescent compound may bind directly or indirectly to the affinity tag. When the fluorescent compound binds directly, the charged chemical moiety or protein of the binding domain interacts directly to form a non-covalent bond between the fluorescent compound and the affinity tag of the fusion protein. When the compounds of the present invention bind indirectly, a metal ion facilitates the indirect binding by having affinity for both the charged amino acid residues of the affinity tag and the binding domain of the fluorescent compound. The indirect binding of the fluorescent compound results in a ternary complex of the fluorescent compound, metal ion and affinity tag of the fusion protein.

The present invention provides specific fluorescent compounds and methods used to detect and label fusion proteins that contain a poly-histidine affinity tag or a poly-arginine affinity tag. These compounds have the general formula A(L)m(B)n wherein A is a fluorophore, L is a linker, B is a binding domain, m is an integer from 1 to 4 and n is an integer from 1 to 6. The linker functions to covalently attach the fluorophore to the binding domain wherein the resulting fluorescent compound contains an acetic acid binding domain. The acetic acid groups interact directly with the positively charged histidine or arginine residues of the affinity tag to effectively label and detect a fusion protein containing such an affinity tag when present in a slightly acidic or neutral environment. Alternatively, the acetic acid groups of the fluorescent compound have an affinity for the metal ions nickel and cobalt wherein the metal ions also have affinity for the poly-histidine affinity tag of the fusion peptide. This indirect labeling and detection of the fusion protein may in certain circumstances be as effective as the direct method that does not utilize the metal ions for labeling and detecting fusion proteins containing poly-histidine affinity tags. The fluorescent compounds of the present invention that have an affinity for poly-histidine affinity tags effectively bind non-covalently when present in a moderately acidic or neutral environment, preferably in a buffer with a pH about 5 to 7.0.

BRIEF DESCRIPTION OF THE FIGURES

FIG. 1.

DETAILED DESCRIPTION OF THE INVENTION

I. Definitions

Figure 1A:
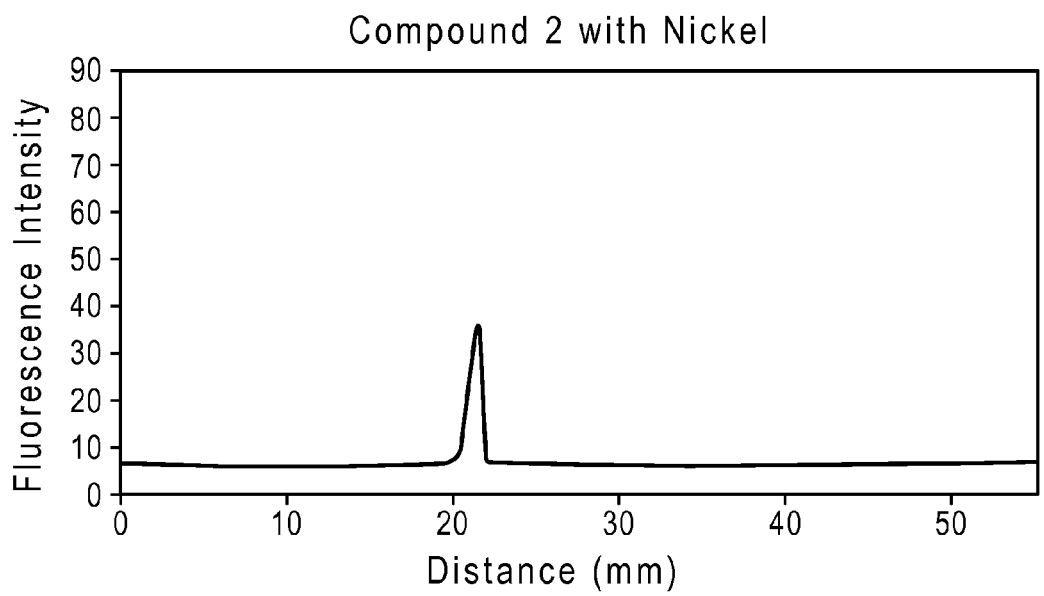
FIG. 1A is a graph demonstrating the detection of a poly-histidine affinity tag containing fusion protein (urate oxidase) labeled with Compound 2 in a staining solution containing nickel ions.

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a fusion protein" includes a plurality of proteins and reference to "a fluorescent compound" includes a plurality of compounds and the like.

Unless defined otherwise, all technical and scientific terms used herein have the same meaning as commonly understood by one of ordinary skill in the art to which this invention is related. The following terms are defined for purposes of the invention as described herein.

The term "acetic acid binding domain" as used herein refers to a domain that contains at least two terminal acetic acid groups, as defined below. The acetic acid binding domains contain nitrogen as the point of attachment for the acetic acid groups and the binding domain is attached to a linker at either a nitrogen or carbon atom depending on one of the three (I, II or III) formulas for the binding domain. Specifically, the acetic acid binding domains have formula (I) $^-O_2CCH(R)N(CH_2CO^-_2)_2$, wherein R is a linker that is covalently bonded to the methine carbon atom (See, for example Compound 1), or formula (II) $-N(CH_2CO_2^-)_2$ wherein the linker is covalently bonded to the nitrogen atom (See, for example Compound 12). Alternatively, the acetic acid binding domain has formula (III) $(CH_2CO^-_2)_ZN[(CH(R))_SN(CH_2CO^-_2)]_T(CH(R))_SN(CH_2CO^-_2)_Z$ wherein the linker is attached to a methine carbon or nitrogen atom and Z is 1 or 2, S is 1 to 5 and T is 0 to 4. In all cases, the acetic acid binding domain contains at least two acetic acid groups and the nitrogen atom is the point of attachment for the acetic acid groups.

The term "acetic acid group" as used herein refers to the chemical formula (IV) $-CH(R)CO^-_2$, which includes the protonated form $-CH(R)CO_2H$. R is independently H or a Linker, as defined below. When R is hydrogen the acetic acid group has the formula $-CH_2CO^-_2$. When the linker of the fluorescent compound is attached to a methine carbon of an acetic acid group then R is the linker. When an acetic acid group is referred to, it is understood to be a terminal end of a compound, which allows for the negatively charged carboxy group of the acetic acid group to freely interact with a positively charged affinity-binding domain. When acetic acid groups are part of the binding domain, nitrogen is the point of attachment for the acetic acid groups. These binding domains are particularly useful for labeling and detecting poly-histidine affinity tags, e.g. $^-O_2CCH(R)N(CH_2CO^-_2)_2$ wherein R is the point of attachment of the Linker.

The term "affinity" as used herein refers to the strength of the binding interaction of two molecules, such as a metal chelating compound and a metal ion or a positively charged moiety and a negatively charged moiety.

The term "affinity tag" as used herein refers to any known amino acid sequence fused to a protein of interest at either the amino terminal or carboxy terminal end of the protein (K. Terpe, Appl. Microbiol. Biotechnol (2003) 60:523-533). Typically, the affinity tag is used for isolation and or detection purposes. The "affinity tag" may optionally be in the middle of the protein of interest such that when the corresponding nucleic acid sequence is translated the affinity tag is fused in frame into the protein of interest. The amino acid residues form a peptide that has affinity for a chemical moiety, a metal ion or a protein. The affinity tag may have an overall positive, negative or neutral charge; typically the affinity tag has an overall positive or negative charge.

The term "affinity-tag-containing-fusion protein" as used herein refers to a fusion protein that contains a protein of interest and an affinity tag.

The term "alkyl" as used herein refers to a straight, branched or cyclic hydrocarbon chain fragment containing between about one and about twenty five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment. Such substitutions include, but are not limited to: aryl; heteroaryl; halogen; alkoxy; amine (—NH); carboxy and thio.

The term "aqueous solution" as used herein refers to a solution that is predominantly water and retains the solution characteristics of water. Where the aqueous solution contains solvents in addition to water, water is typically the predominant solvent.

The term "B binding domain", "B" and "binding domain" as used herein refer to a component of the fluorescent compound that interacts directly or indirectly with the affinity tag of the fusion protein. The binding domain can be a chemical moiety that has an overall charge or a protein, provided the protein is not an antibody or a fragment thereof. The binding domain may be substituted to adjust the binding affinity, solubility or other physical properties of the fluorescent compound that the binding domain is covalently attached to. An important aspect of the invention is that the binding domain does not contain an arsenic atom.

The term "benzofuran" as used herein refers to a fluorophore generally having the structure below and derivatives thereof.

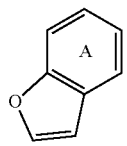

The benzofuran is typically attached to a 1,2-bis(2-aminophenoxy)ethane-N,N,N',N'-tetraacetic acid (BAPTA) metal chelating group by a single covalent bond at any carbon atom of the BAPTA compound or as a fused ring wherein ring A on the benzofuran would also be one of the two aromatic carbon rings of the BAPTA compound. The benzofuran may optionally be further substituted or unsubstituted as depicted below.

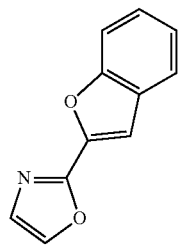 [SMILES: c1ccc2oc(-c3ncco3)cc2c1]

The fluorophore may also be further substituted by substituents that adjust the binding solubility, spectral properties or other physical properties of the fluorophore.

The term "borapolyazaindacene" as used herein refers to a fluorophore generally having the formula and derivatives thereof

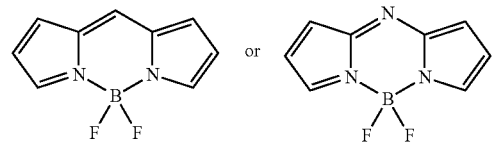

The fluorophore is covalently attached by a linker to at least one binding domain such as an acetic acid binding domain to form a compound of the present invention. The fluorophore may also be further substituted by substituents that adjust the solubility, spectral properties or other physical properties of the fluorophore The term "buffer" as used herein refers to a system that acts to minimize the change in acidity or basicity of the solution against addition or depletion of chemical substances.

The term "calmodulin" as used herein refers to a binding domain that when complexed with calcium binds the calmodulin affinity tag.

The term "calmodulin affinity tag" as used herein refers to the amino acid sequence that codes for calmodulin binding peptide and includes any corresponding peptides disclosed in U.S. Pat. Nos. 5,585,475; 6,117,976 and 6,316,409. The "calmodulin affinity tag" is fused to a protein of interest for the purposes of detection and purification.

The term "coumarin" as used herein refers to a fluorophore generally having the structure below and derivatives thereof, wherein A is OR' or N(R')$_2$ wherein R' is hydrogen or alkyl

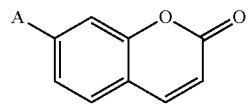

The fluorophore is covalently attached by a linker to at least one binding domain, such as an acetic acid binding domain, to form a compound of the present invention. The fluorophore may also be further substituted by substituents that adjust the solubility, spectral properties or other physical properties of the fluorophore.

The term "complex" as used herein refers to the association of two or more molecules, usually by non-covalent bonding, e.g., the association between the negatively charged acetic acid groups and the positively charged histidine residues of a poly-histidine affinity tag.

The term "detectable response" as used herein refers to an occurrence of, or a change in, a signal that is directly or indirectly detectable either by observation or by instrumentation. Typically, the detectable response is an occurrence of a signal wherein the fluorophore is inherently fluorescent and does not produce a significant change in signal upon binding to a metal ion or biological compound. Alternatively, the detectable response is an optical response resulting in a change in the wavelength distribution patterns or intensity of absorbance, fluorescence or a change in light scatter, fluorescence lifetime, fluorescence polarization, or a combination of the above parameters.

The term "direct binding" as used herein refers to binding of the fluorescent compound to the affinity tag of the fusion protein with the proviso that a metal ion does not comprise the resulting complex. Typically the charged binding domain of the fluorescent compound has an affinity for the charged amino acid residues of the affinity tag wherein a stable non-covalent bond is formed between the compound and peptide.

The term "FLAG affinity tag" as used herein refers to the amino acid sequence DYKDDDDK and any corresponding peptide disclosed in U.S. Pat. Nos. 4,851,341 and 5,011,912, wherein the FLAG affinity tag is fused to a protein of interest.

The term "fluorescent compound" as used herein refers to a compound with the general formula A(B)n wherein A is a fluorophore, B is a binding domain comprising a chemical moiety, protein or fragment thereof that is capable of binding, directly or indirectly, to the affinity tag of the fusion protein wherein n is an integer from about 1 to about 6, with the proviso that the fluorescent compound does not comprise an antibody or fragment thereof. When the binding domain is a chemical moiety the fluorescent compound has the general formula A(L)m(B)n wherein L is a Linker that covalently attaches the fluorophore to the binding domain. The fluorescent compound of the present invention effectively non-covalently attaches a fluorophore to the fusion protein at the site of the affinity tag.

The term "fluorophore" as used herein refers to a compound that is inherently fluorescent or demonstrates a change in fluorescence upon binding to a biological compound or metal ion, i.e., fluorogenic. Numerous fluorophores are known to those skilled in the art and include, but are not limited to, coumarin, cyanine, acridine, anthracene, benzofuran, indole, borapolyazaindacene and xanthenes including fluorescein, rhodamine and rhodol as well as other fluorophores described in RICHARD P. HAUGLAND, MOLECULAR PROBES HANDBOOK OF FLUORESCENT PROBES AND RESEARCH CHEMICALS ($9^{th}$ edition, CD-ROM, 2002).

The term "fusion protein" as used herein refers to a protein hybrid containing an affinity tag and a protein of interest or any amino acid sequence of interest. The affinity tag may be directly linked or indirectly linked to the fusion protein. When the affinity tag is indirectly linked there is preferably a cleavage site between the affinity tag and the protein of interest that facilitates recovery of the protein of interest free from the affinity tag. When a fusion protein containing a cleavage site comes into contact with an appropriate protease that is specific for the cleavage site, such as enterokinase, the fusion protein is cleaved into two polypeptides: the affinity tag and the protein of interest.

The term "Glu-Glu affinity tag" as used herein refers to the amino acid sequence EEEEYMPME or a fragment thereof that is fused to a protein of interest, either at an end or within the protein.

The term "glutathione" as used herein refers to a tripeptide, or derivative thereof, that specifically binds to the GST affinity tag and when part of a fluorescent compound of the present invention represents the binding domain of the fluorescent compound. Typically, "glutathione" refers to the tripeptide γ-glutamylcysteinylglycine, Glu-(Cys-Gly).

The term "GST affinity tag" as used herein refers to an amino acid sequence that encodes for all or part of glutathione S-transferase including any corresponding polypeptides disclosed in U.S. Pat. No. 5,654,176, that is fused to a protein of interest.

The term "halogen" as used herein refers to the substituents fluoro, bromo, chloro, and iodo.

The term "poly-histidine affinity tag" as used herein refers to a non-natural consecutive sequence of histidine amino acid residues including any corresponding peptides disclosed in U.S. Pat. Nos. 5,284,933 and 5,310,663. Typically such sequences comprise four to ten histidine residues that are typically linked to the carboxy and/or amino terminal end of a protein of interest. Optionally, the poly-histidine affinity tag may be linked, in-frame, in the middle of the protein of interest.

The term "indirect binding" as used herein refers to the binding of the fluorescent compound to the affinity tag due to a third component, typically a polyvalent metal ion. The fluorescent compound and the affinity tag form a ternary complex with a metal ion wherein the metal ion binds both the affinity tag and the acetic acid groups of the fluorescent compound. The metal ion has affinity for both the binding domain and affinity tag and as such confers affinity to the binding domain for the affinity tag that would not be present without the metal ion. Alternatively, a metal ion has affinity for the binding domain that when bound induces a conformational change that confers affinity to the binding domain for the affinity tag. Thus, in this instance, the metal ion may not have affinity for the affinity tag; however, the metal ion will induce the binding domain to have affinity for the affinity tag.

The term "indole" or "indole derivative" as used herein refers to a compound generally having the formula and derivatives thereof.

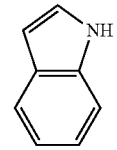

The fluorophore is substituted by a linker at any of the aromatic carbon atoms and the linker attaches the fluorophore to a binding domain. The fluorophore may also be further substituted by substituents that adjust the solubility, spectral properties or other physical properties of the fluorophore.

The term "isolated," as used herein refers to, a preparation of peptide, protein or protein complex that is essentially free from contaminating proteins that normally would be present in association with the peptide, protein or complex, e.g., in a cellular mixture or milieu in which the protein or complex is found endogenously. In addition "isolated" also refers to the further separation from reagents used to isolate the peptide, protein or complex from cellular mixture. Thus, an isolated fusion protein may be isolated from cellular components and optionally from the fluorescent compounds of the present invention that normally would contaminate or interfere with the study of the complex in isolation, for example while screening for modulators thereof.

The term "kit" as used refers to a packaged set of related components, typically one or more compounds or compositions.

The term "Linker" or "L" as used herein refers to a single covalent bond or a series of stable covalent bonds incorporating 1-30 nonhydrogen atoms selected from the group consisting of C, N, O, S and P that covalently attach the fluorophore to the binding domain of the fluorescent compounds.

The term "metal chelator" or "metal chelating moiety" as used herein refers to a chemical compound that combines with a metal ion to form a chelate structure.

The term "metal ion" as used herein refers to any metal ion that has an affinity for an affinity tag and/or a binding domain and that can be used to indirectly complex the fluorescent compound and the fusion protein together. Such metal ions include, but are not limited to, $Ni^{2+}$, $Co^{2+}$, $Zn^{2+}$, $Cu^{2+}$, $Al^{3+}$, $Ca^{2+}$, $Ac^{3+}$, $Fe^{3+}$ and $Ga^{3+}$.

The term "NTA" as used herein refers to the metal chelating group Nα, Nα-bis(carboxymethyl)-lysine and derivatives thereof. Such derivatives include nitriloacetic acid.

The term "poly-arginine affinity tag" as used herein refers to a consecutive sequence, typically 4-6, of arginine residues (Nock et al (1997) FEBS Lett. 414(2):233-238).

The terms "protein" and "polypeptide" are used herein in a generic sense to include polymers of amino acid residues of any length. The term "peptide" is used herein to refer to polypeptides having less than 250 amino acid residues, typically less than 100 amino acid residues. The terms apply to amino acid polymers in which one or more amino acid residues are an artificial chemical analogue of a corresponding naturally occurring amino acid, as well as to naturally occurring amino acid polymers.

The term "protein of interest" as used herein refers to any protein to which an affinity tag is fused to for the purpose of detection, isolation, labeling, tagging, monitoring and purification.

The term "sample" as used herein refers to any material that may contain fusion proteins, as defined above. Typically, the sample comprises endogenous host cell proteins. The sample may be in an aqueous solution, a viable cell culture or immobilized on a solid or semi solid surface such as a polymeric gel, polymeric bead, membrane blot or on a microarray.

II. Compositions and Methods of Use

In accordance with the present invention, methods and compositions are provided that label and detect fusion proteins by specifically and selectively binding to an affinity tag of a fusion protein. The affinity tag is defined to include any affinity tag known to one skilled in the art and fused to a protein of interest for the purposes of detection and purification. The fluorescent compound is defined as being capable of binding to an affinity tag and includes the general formula A(B)n wherein A is any fluorophore known to one skilled in the art, B is a selected binding domain of the present invention and n is an integer from 1 to 6. The binding domain is a chemical moiety, protein or fragment thereof with the proviso that the fluorescent compound does not comprise an antibody or fragment thereof. The binding domain may interact directly, selectively binding to the affinity tag, or indirectly, wherein a third component forms a ternary complex between the fluorescent compound and the affinity tag. Typically, the third component is a metal ion wherein the metal ion has affinity for both the affinity tag and the binding domain. Alternatively, the third component does not have an affinity for the affinity tag but induces a conformational change to the binding domain such that the binding domain has an affinity for an affinity tag. The binding moiety can be a charged chemical moiety such as a metal chelating group, a protein, a peptide or fragment thereof such as calmodulin, provided that the binding domain is not an antibody or generated from an antibody. Thus, the present invention contemplates a wide range of fluorescent compounds that can be used to detect a myriad of affinity tags that are fused to a protein of interest whereby detection of a fusion protein is determined by a fluorescent signal generated from the fluorescent compound.

In addition to the components of the fluorescent compound that confer selectivity for an affinity tag, the staining solution also plays a critical role in determining selectivity and is typically altered depending on the affinity tag and the assay method. The staining solution contains a buffer and a fluorescent compound wherein the buffering components fine-tune the selectivity of the fluorescent compound for an affinity tag. For example, we have found that for the selective detection of poly-histidine containing fusion proteins on a gel that the buffer is preferably slightly acidic or neutral, contains a salt and has a pKa of about 6.0 to about 7.05. It appears that a pKa value of the buffer that is similar to the pKa value of the imidazole ring of histidine, which is about 7.05, results in a buffer that facilitates the non-covalent binding of the fluorescent compound to the poly-histidine affinity tag. Thus, preferred buffers for the detection of poly-histidine affinity tag containing fusion proteins includes, but are not limited to, Good's buffer, PIPES and MOPS buffers.

A. Components of the Fluorescent Compounds

The present invention provides fluorescent compounds that have an affinity for a number of affinity tags. When the binding domain is a protein, typically there is a short linker, less than 10 nonhydrogen atoms that covalently attach the fluorophore to the protein-binding domain. The protein-binding domain may interact directly or indirectly through a metal ion with the affinity tag. When the binding domain is a charged chemical moiety the fluorescent compounds of the present invention have the general formula A(L)m(B)n wherein A is a fluorophore, L is a Linker, B is a binding domain, m is an integer from 1 to 4 and n is an integer from 1 to 6. By selection of an appropriate binding domain, a corresponding affinity tag can be selectively and non-covalently labeled with a fluorophore. The fluorophore typically has a passive role in the affinity of the binding domain for the affinity tag, although the fluorophore may be substituted to alter the affinity of the covalently attached binding domain. However, we have found that fluorophores that are substituted by sulfonated groups tend to reduce the selectivity of the fluorescent compound for the affinity tag. Therefore, one skilled in the art will appreciate that any fluorophore, or derivative thereof, can be covalently linked using an appropriate Linker(s) to a specific binding domain resulting in a significant advancement in the ability to fluorescently detect fusion proteins that contain an affinity tag.

1. Fluorophores of the Fluorescent Compounds

A fluorophore of the present invention is any chemical moiety that exhibits an absorption maximum beyond 280 nm, and when covalently linked to a binding domain of the present invention forms a fluorescent compound. The covalent linkage can be a single covalent bond or a combination of stable chemical bonds. The covalent linkage attaching the fluorophore to the binding domain is typically a substituted alkyl chain that incorporates 1-30 nonhydrogen atoms selected from the group consisting of C, N, O, S and P. Optionally, the linker can be a single covalent bond or the alkyl chain can incorporate a benzene ring.

Fluorophores of the present invention include, without limitation; a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine (including any corresponding compounds in U.S. Pat. No. 5,863,753), a carbocyanine (including any corresponding compounds in U.S. Ser. Nos. 09/557,275; 09/968,401 and 09/969,853 and U.S. Pat. Nos. 6,403,807; 6,348,599; 5,486,616; 5,268,486; 5,569,587; 5,569,766; 5,627,027 and 6,048,982), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343, 5,798,276 and U.S. Ser.

No. 09/922,333), an oxazine or a benzoxazine, a carbazine (including any corresponding compounds disclosed in U.S. Pat. No. 4,810,636), a phenalenone, a coumarin (including an corresponding compounds disclosed in U.S. Pat. Nos. 5,696, 157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

Where the fluorophore is a xanthene, the fluorophore is optionally a fluorescein, a rhodol (including any corresponding compounds disclosed in U.S. Pat. Nos. 5,227,487 and 5,442,045), or a rhodamine (including any corresponding compounds in U.S. Pat. Nos. 5,798,276 and 5,846,737). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171).

Preferred fluorophores of the invention include xanthene, coumarin, cyanine, acridine, anthracene, benzofuran, indole and borapolyazaindacene. Most preferred are cyanine, borapolyazaindacene, coumarin and benzofuran. The choice of the fluorophore attached to the binding domain will determine the fluorescent compound's absorption and fluorescence emission properties. It is an aspect of the present invention that the fluorophore not be sulfonated.

2. Linkers of the Fluorescent Compounds

As described above, the fluorophores of the present invention are covalently attached to a binding domain by a Linker to form the fluorescent compounds of the present invention. The Linker typically incorporates 1-30 nonhydrogen atoms selected from the group consisting of C, N, O, S and P. The linker is typically a substituted alkyl or a substituted cycloalkyl. Alternately, the fluorophore may be directly attached (where Linker is a single bond) to the binding domain or the alkyl may contain a benzene ring. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the linker incorporates less than 20 nonhydrogen atoms and are composed of any combination of ether, thioether, urea, thiourea, amine, ester, carboxamide, sulfonamide, hydrazide bonds and aromatic or heteroaromatic bonds. Typically the linker is a combination of single carbon-carbon bonds and carboxamide, sulfonamide or thioether bonds. The bonds of the Linker typically result in the following moieties that can be found in the Linker: ether, thioether, carboxamide, thiourea, sulfonamide, urea, urethane, hydrazine, alkyl, aryl, heteroaryl, alkoky, cycloalkyl and amine moieties. Examples of typical fluorescent compounds incorporate the following three (V, VI and VII) Linker formulas: Formula (V) —$(CH_2)_eC(X)NH(CH_2)_e(NHC(X)(CH_2)_e)_d$—, Formula (VI) —$((C_6R''_4)O)_d(CH_2)_e(C(X)NH(CH_2)_e)(NH)_dC(X)NH(C_6R''_4)(CH_2)_e$— and Formula (VII) —$(O)_d(CH_2)_fO(C_6R''_4)$— wherein X is O or S, d is 0-1, e is 1-6, f is 2 or 3, and R" is independently H, halogen, alkoxy or alkyl. It is understood that X, d, e and are independently selected within a linker.

Thus, a selected embodiment of the present invention is the following fluorescent compound formulas (VIII, IX and X): Formula (VIII) (A)-$[(CH_2)_eC(X)NH(CH_2)_e(NHC(X)(CH_2)_e)_d]_m$—$(B)_n$; Formula (IX) (A)-$((C_6R''_4)O)_e(CH_2)_e(C(X)NH(CH_2)_e)(NH)_dC(X)NH(C_6R''_4)(CH_2)_e$—(B) and Formula (X) (A)-$(O)_d(CH_2)_fO(C_6R''_4)$—(B) wherein m is an integer from 1 to 4, m is an integer from 1 to 6, A is a fluorophore and B is a binding domain. Particularly preferred is Formula (VIII) wherein d is 0, e is 1 to 4, X is O, m is 2 and n is 2 or Formula (VIII) wherein d is 1 and e is 1 or 2. Preferred embodiments of Formula (X) is when d is 0, f is 2, or a variation of Formula (X) having the Formula (XI) (B)(L)(A)-$(O)_d(CH_2)_fO(C_6R''_4)$—(B) wherein L is a single covalent bond, B is a binding domain, A is a fluorophore, d is 1 and f is 2.

Any combination of linkers may be used to attach the fluorophore and the binding domain together, typically a fluorophore will have one or two linkers attached that may be the same or different. In addition, a linker may have more than one binding domain per linker. The linker may also be substituted to alter the physical properties of the fluorescent compound, such as binding affinity of the binding domain and spectral properties of the fluorophore. For fluorescent compounds that have an affinity for the poly-histidine affinity tag, the linker typically incorporates an oxygen atom due to its ability to increase the affinity of the acetic acid binding domain, described below, for the affinity tag. This feature of the linker is especially true for fluorescent compound Formula (XI) (B)(L)(A)-$(O)_d(CH_2)_fO(C_6R''_4)$—(B). Thus, an important feature of the linker is to alter the binding affinity of the binding domain by increasing the affinity with the incorporation of oxygen into the linker.

The linker can also have other substituents that alter the binding affinity of the binding domain. The benzene ring $(C_6R''_4)$ of Formula (XI) is typically substituted with a halogen, preferably chlorine or fluorine, which tune the affinity of the binding domain. These halogen substituents appear to lower the affinity of binding domain but increase the specificity of the binding domain for the affinity tag resulting in overall increased sensitivity of the fluorescent compound for the affinity tag. Thus, linker substituents function to tune the binding affinity of the fluorescent compound to optimize the sensitivity of the binding domain for the affinity tag Another important feature of the linker is to provide an adequate space between the fluorophore and the binding domain so as to prevent the fluorophore from providing a steric hindrance to the binding of the affinity tag for the binding domain of the fluorescent compound. Thus, when a binding domain is attached to the fluorophore by a single covalent bond there is typically another linker containing an oxygen atom attached to the same fluorophore at a different position to increase the affinity of both binding domains for the affinity tag. Therefore, the linker of the present fluorescent compounds is important for (1) coupling the fluorophore to the binding domain, (2) providing an adequate space between the fluorophore and the binding domain so as not to sterically hinder the affinity of the binding domain and the affinity tag and (3) altering the affinity of the binding domain for the affinity tag either by the choice of the atoms of the linker or indirectly by addition of substituents to the linker.

3. Binding Domains of the Fluorescent Compounds

The binding domain of the present fluorescent compounds, include without limitation, charged chemical moieties, a proteins or fragments thereof that are capable of non-covalently binding to an affinity tag of the present invention. The binding domain, either independently or when complexed with a metal ion, has specific and selective affinity for an affinity tag containing fusion protein. The fluorescent compounds, A(L)
m(B)n, may have more than one linker and more than one
binding domain, which may or may not be the same. Preferably, the binding domains are all selective for the same affinity tag, however for certain applications it may be desirable to
have one fluorophore linked to binding domains that have
selective affinity for different affinity tags. In this manner,
selection and orientation of the binding domain relative to the
fluorophore is critical for the specificity, sensitivity and selectivity of the binding domain.

The present invention contemplates protein and peptide-binding domains that are not antibodies or fragments thereof.
Thus, an aspect of the present invention is affinity tags that are
selective for such proteins, and these include without limitation, GST, calmodulin, maltose-binding, and chitin-binding
affinity tags. These peptides bind the glutathione tripeptide,
calmodulin protein, maltose and chitin respectively. When
these polypeptides are attached by a linker to a fluorophore,
they function to site-specifically label these affinity tag containing fusion proteins.

Calmodulin selectively and with high affinity binds calcium ions, the calcium ions then induce a conformation
change that causes the protein to have affinity for the calmodulin affinity tag (Hentz N G et al. (1996) Anal Chem
68:1550-5; Zheng C F et al. (1997) 186:55-60). A fluorophore
of the present invention that is covalently attached to calmodulin effectively attaches the fluorophore to the calmodulin
affinity tag and subsequently a protein of interest. Thus, a
staining solution specific for calmodulin affinity tag containing fusion proteins would include, at a minimum, a fluorescent compound comprising calmodulin and calcium ions.

In contrast, the glutathione tripeptide binds directly to the
GST affinity tag (Kaplan W et al (1997) Protein Sci. 6:399-406; Lew A M et al (1991) J. Immunol. Methods 136:211-9).
A fluorescent compound covalently attached to glutathione
effectively attaches a fluorophore to a GST affinity tag containing fusion protein. In this way, fluorescent compounds
comprising glutathione, provide an effective means for
detecting such fusion proteins in a gel or solution, a means not
previously feasible with currently known compounds, See
Example 20. Thus, an aspect of the invention is detection of
GST affinity tag containing fusion proteins with a fluorescent
compound that comprises the tripeptide glutathione. Preferred fluorescent compounds comprise a xanthene fluorophore.

An important aspect of the present invention includes
charged chemical moieties that have affinity for an affinity
peptide. These moieties include, without limitation, acetic
acid groups, phosphates and sulfates. Particularly preferred
are binding domains that have affinity for positively charged
affinity tags such as poly-histidine or poly-arginine affinity
tag containing fusion proteins. These binding domains typically contain terminal acetic acid groups. The acetic acid
binding domains contain nitrogen as the point of attachment
for the acetic acid groups and the binding domain is attached
to a linker at either a nitrogen or carbon atom depending on
one of the three (I, II or III) formulas for the binding domain.
Specifically, the acetic acid binding domains have formula
(I) $^-O_2CCH(R)N(CH_2CO_2)_2$, wherein R is a linker that is
covalently bonded to the methine carbon atom (See, for
example Compound 1), or formula (II) —$N(CH_2CO_2)_2$
wherein the linker is covalently bonded to a nitrogen atom
(See, for example Compound 12). Alternatively, the acetic
acid binding domain has formula (III) $(CH_2CO^-_2)_Z N[(CH(R))_S N(CH_2CO^-_2)]_T (CH(R))_S N(CH_2CO^-_2)_Z$ wherein the
linker is attached to a methine carbon or nitrogen atom and Z
is 1 or 2, S is 1 to 5 and T is 0 to 4. In all cases, the acetic acid
binding domain contains at least two acetic acid groups and a
nitrogen atom is the point of attachment for the acetic acid
groups. When a binding domain that contains only two acetic
acid groups is attached to a fluorophore either (1) another
acetic acid binding domain is also attached to the fluorophore
or (2) an acetic acid group is attached by a linker to the
fluorophore. This is because the fluorescent compounds with
at least three acetic acid groups is preferable for providing
selective and sensitive affinity for the poly-histidine affinity
tag.

The acetic acid binding domains are typically part of a
metal chelating moiety such as BAPTA, IDA, NTA, DTPA
and TTHA. BAPTA, as used herein, refers to analogs, including derivatives, of the metal chelating moiety (1,2-bis(2-aminophenoxy)ethane-N,N,N',N'-tetraacetic acid) and salts
thereof including any corresponding compounds disclosed in
U.S. Pat. Nos. 4,603,209; 4,849,362; 5,049,673; 5,453,517;
5,459,276; 5,516,911; 5,501,980; and 5,773,227. IDA, as
used herein, refers to imidodiacetic acid compounds and
derivatives thereof. DTPA, as used herein, refers to diethylenetriamine pentaacetic acid compounds and derivatives
thereof including any corresponding compounds disclosed in
U.S. Pat. Nos. 4,978,763 and 4,647,447. NTA, as used herein,
refers to Nα,Nα-bis(carboxymethyl)-lysine and derivatives
thereof, such derivatives including nitriloacetic acid. TTHA,
as used herein, refers to triethylenetetramine hexaacetic acid
and derivatives thereof.

The acetic acid binding domain may comprise the entire
metal chelating moiety or only be part of such a moiety. A
binding domain that encompasses an entire chelating moiety
is represented by the formulas (I) $^-O_2CCH(R)N(CH_2CO^-_2)_2$,
and (III) $(CH_2CO^-_2)_Z N[(CH(R))_S N(CH_2CO^-_2)]_T N(CH(R))_S N(CH_2CO^-_2)_Z$ wherein these formulas comprise the chelating moieties NTA (Formula I), DTPA and TTHA (Formula
III). The binding domain having the formula (II)
$N(CH_2CO_2)_2$ comprises, in part, the chelating moieties IDA
and BAPTA. When a binding domain is only part of a chelating moiety such as BAPTA, the remaining part of the chelating moiety comprises the linker of a fluorescent compound or
the fluorophore. This is demonstrated by the fluorescent compound Formula (X) $(A)-(O)_d(CH_2)_fO(C_6R''_4)$—(B), wherein
the represented linker is part of the BAPTA chelating moiety.
The remaining phenyl ring of the BAPTA moiety, when
present, is typically part of the fluorophore, as demonstrated
by Compound 12.

Due to the inclusion of chelating moieties in the binding
domain and/or linker of the fluorescent compounds these
moieties can be optionally substituted to adjust the binding
affinity, solubility, or other physical properties of the compound. This is particularly true for the BAPTA chelating
moiety wherein the benzene ring ($C_6R''_4$) of the linker Formula (VII) —$(O)_d(CH_2)_fO(C_6R''_4)$— is optionally substituted. Particularly advantageous substitutions are halogen
substituents, especially fluorine and chlorine. Without wishing to be bound by a theory, it appears that these substituents,
as electron withdrawing groups, tune the affinity of the binding domain for the affinity tag or a metal ion resulting in
increased stability of the complex.

Figure 1B:
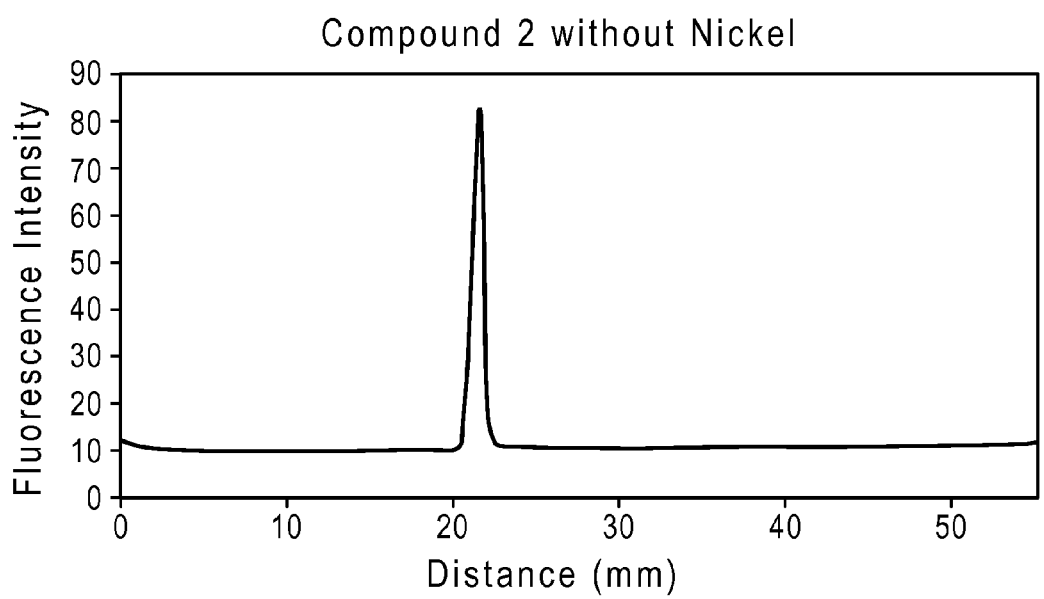
FIG. 1B is a graph showing data from the same experiment performed without nickel ions. In this particular assay, Compound 2 demonstrates an increased sensitivity for the poly-histidine affinity tag in the absence of nickel ions.
Figure 2A:
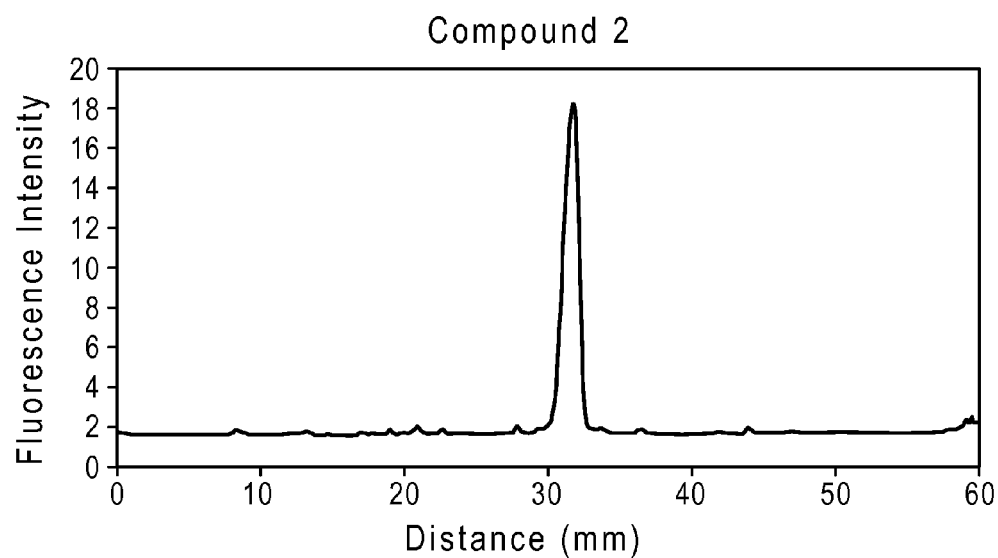
FIG. 2A is a graph showing the detection of a poly-histidine affinity tag containing fusion protein (Oligomycin sensitivity conferring protein; OSCP) labeled with Compound 2 in a staining solution containing nickel ions followed by the detection of (shown in FIG. 2B) total protein using the total protein stain SYPRO® Ruby. This assay demonstrates that Compound 2 is selective for the poly-histidine affinity tag.
Figure 2B:
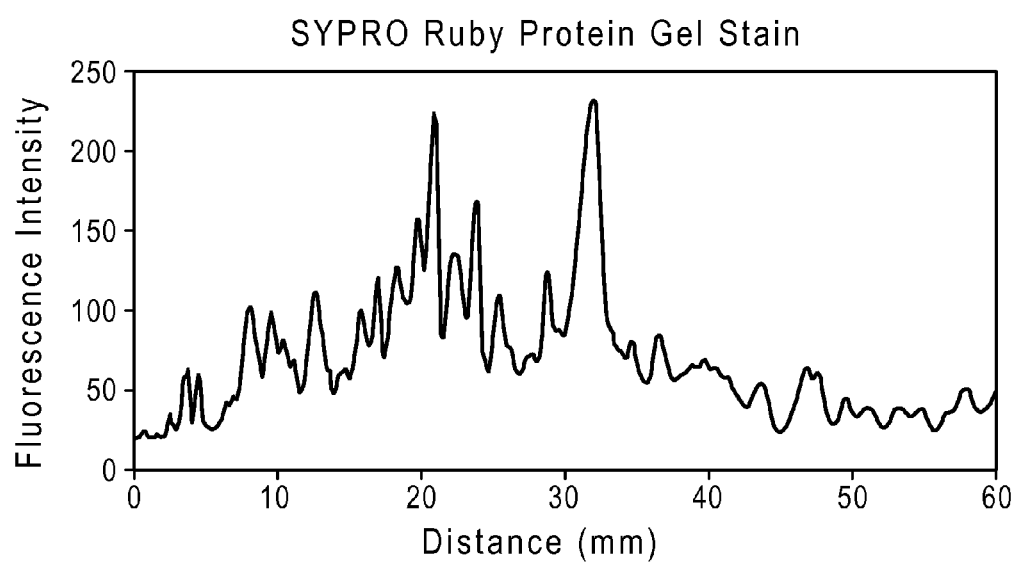
FIG. 2.
Figure 3A:
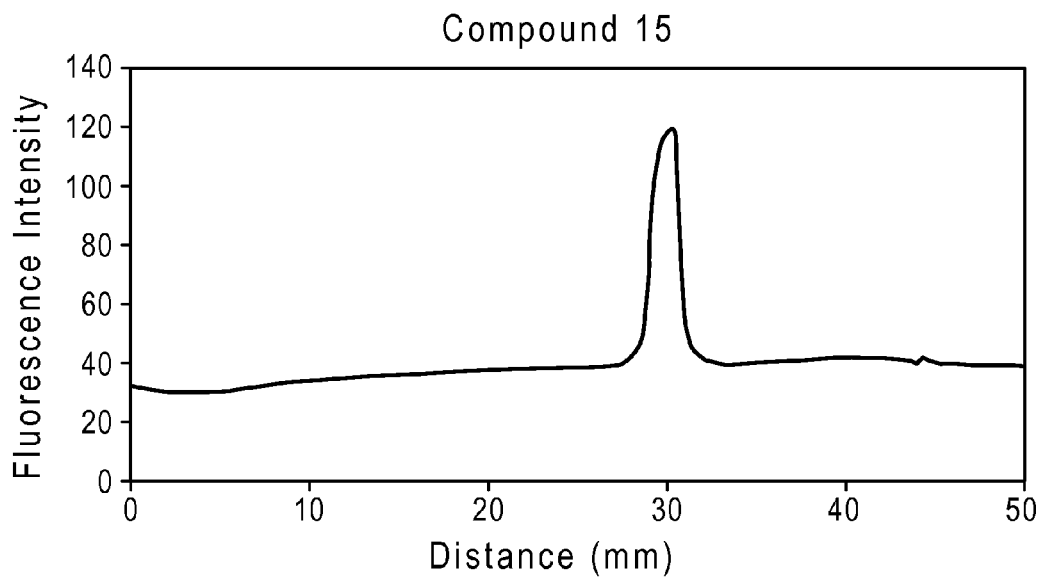
FIG. 3A is a graph showing the detection of a poly-histidine affinity tag containing fusion protein (Oligomycin sensitivity conferring protein; OSCP) labeled with Compound 15 in a staining solution containing nickel ions followed by the detection of (shown in FIG. 3B) total protein using the total protein stain SYPRO® Ruby. This assay demonstrates that Compound 15 is selective for the poly-histidine affinity tag.
Figure 3B:
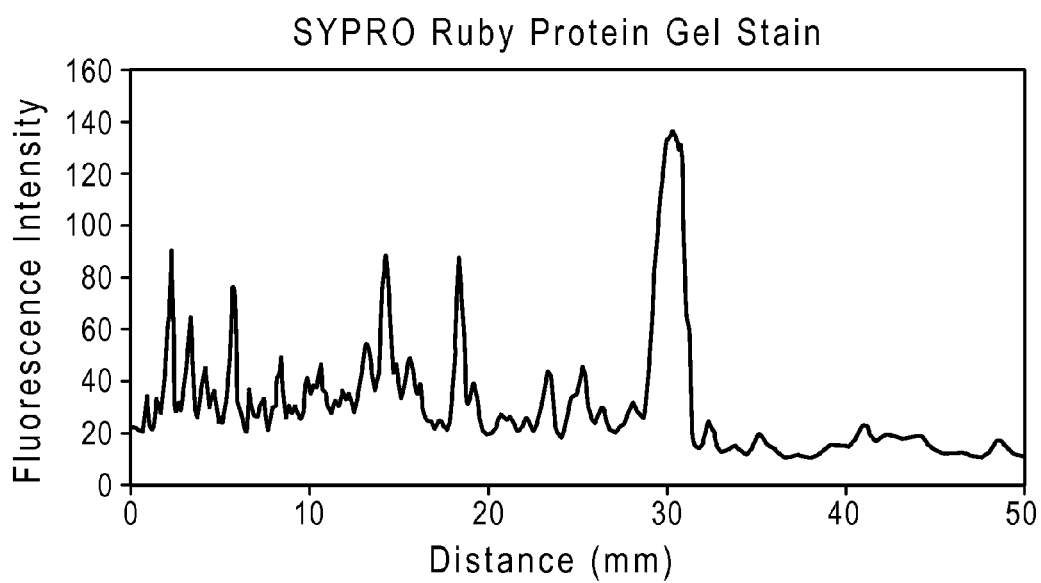
FIG. 3.

In addition, because the acetic acid binding domain contains all or part of a number of chelating moieties these
binding domains also have affinity for metal ions. This aspect
of the binding domain is useful for certain fluorescent compounds. However we have unexpectedly discovered that
nickel ions are not necessary for the detection of poly-histidine affinity tag containing fusion proteins (FIG. 1). While
this is an important aspect of the present invention, for some
compounds, inclusion of the metal ion in a staining solution
may be desirable. This is because for certain compounds,
inclusion of metal ions into a staining solution may stabilize
the complex of the fluorescent compound and the affinity tag
containing fusion protein. Thus, for certain compounds, the
inclusion of a metal ion is beneficial. Alternatively, as demonstrated in FIGS. 1 and 2, the acetic acid binding domain has selective affinity for the poly-histidine affinity tag due to the negative charge of the acetic acid groups and the positive charge of the poly-histidine affinity tag at a neutral or mildly acidic pH, and in fact, as FIG. 1 demonstrates an increase in signal intensity is obtained when the staining solution does not contain nickel ions.

B. Combination of Components to Form Fluorescent Compounds

The components of the fluorescent compound having now been described, combination of certain fluorophores, linkers and binding domains are provided to demonstrate the complexity of the fluorescent compounds and their application. While it has been stressed that a wide range of components can be used to make the fluorescent compounds it should also be understood that the individual selection of components to make a particularly useful fluorescent compound requires an understanding of the fluorophores, the linkers, the binding domain and how certain combinations function to selectively bind to affinity tags. Therefore, what follows are selected fluorophores indicating sites of attachment, substituents and preferred linkers along with binding domains. However, the following description is in no way limiting and should not be construed as the only preferred embodiments as many fluorophores with linkers attached are equally as preferred. It is understood that the following compounds comprise the salts, acids and lipophilic forms including esters of the compounds, as particular forms are advantageous in certain applications. Compounds that comprise acetyloxy methyl (AM) ester are particularly useful for intracellular labeling of affinity tag containing fusion proteins wherein fluorescent compounds comprising AM ester moieties easily enter cells where the ester is cleaved resulting in terminal acetic acid groups on the fluorescent compound. In this way, newly translated fusion proteins can be detected, in vivo, and monitored to ascertain information about the functional proteome of the cell including discovery of drug targets. The terminal acetic acid groups are typically part of the binding domain but they may be other places on the compound.

The linkers of the present invention can be attached at many positions on the fluorophore resulting in an exponential number of fluorescent compounds contemplated by the present invention. Preferred fluorophores of the fluorescent compounds are cyanine, coumarin, borapolyazaindacene, benzofuran and xanthenes including rhodol, rhodamine, fluorescein and derivatives thereof.

Most preferred fluorophores of the fluorescent compounds are coumarin and borapolyazaindacene. The coumarin fluorophore has the Formula (XII), as shown below, wherein A is $NH_2$, $OR'$ or $N(R')_2$, $R'$ is H, an alkyl or an acetic acid binding domain and $R^9$-$R^{12}$ and $R^8$ can be any of the corresponding substituents disclosed in U.S. Pat. Nos. 5,696,157 and 5,830,912, supra. Typical substituents include halogen, lower alkyl, alkoxy and hydrogen.

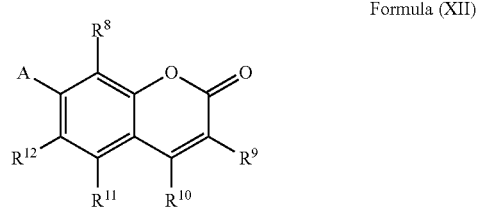

Formula (XII)

Particularly preferred fluorescent compounds with coumarin as a fluorophore are exemplified in compounds 1, 4, 5 and 6. These exemplified compounds comprise a linker at $R^9$ or $R^{10}$ having the formula —$(CH_2)_eC(X)NH(CH_2)_e(NHC(X)(CH_2)_e)_d$— wherein $R^9$ or $R^{10}$ that is not a linker is typically a methyl group, $R^{11}$ is typically hydrogen, $R^{12}$ is fluorine (compound 4), sulfonic acid (compound 1) or hydrogen (compound 5 and 6). $R^{12}$ is typically hydrogen, however a preferred substituent is fluorine (compound 4). Thus, a preferred compound of the present invention has Formula (VIII) (A)-[$(CH_2)_eC(X)NH(CH_2)_e(NHC(X)(CH_2)_e)_d]_m$—$(B)_n$ wherein A is a coumarin, B is an acetic acid binding domain and d of the linker is typically 0.

Alternatively, the coumarin of Formula (XII) can be any of the compounds disclosed in U.S. Pat. Nos. 5,459,276 and 5,501,980. These compounds comprise a linker at $R^{12}$ and the fluorescent compound Formula (XI) (B)(L)(A)-$(O)_d(CH_2)_fO(C_6R''_4)$—(B) wherein (B)(L) is A of fluorophore Formula (XII).

It is understood that the linkers of the present invention may be attached at any of $R^8$-$R^{12}$, and that any of the binding domains of the present invention can be attached to the linker.

The borapolyazaindacene fluorophore has the formula (XIII), as shown below, wherein $R^1$-$R^7$ can be substituted by any of the corresponding substituents disclosed in U.S. Pat. Nos. 5,187,288; 5,248,782 and 5,274,113, supra. Typical substituents include heteroaryl, aryl, lower alky, alkoxy and hydrogen.

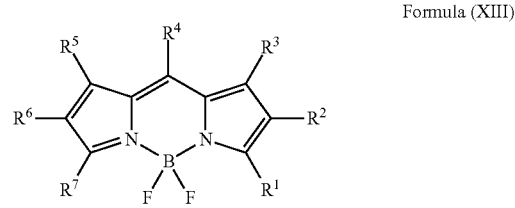

Formula (XIII)

Particularly preferred fluorescent compounds with borapolyazaindacene as a fluorophore are exemplified in compounds 2, 3 and 7-14. These exemplified compounds comprise a linker at $R^7$, $R^6$, $R^2$ or $R^1$ having the Formula (VI) —$((C_6R''_4)O)_d(CH_2)_e(C(X)NH(CH_2)_e)(NH)_dC(X)NH(C_6R''_4)(CH_2)_e$— and/or Formula (V) —$(CH_2)_eC(X)NH(CH_2)_e(NHC(X)(CH_2)_e)_d$—, wherein the fluorophore is attached by one linker or two linkers. When the fluorophore is attached by two linkers, the linkers are typically present at $R^6$ and $R^2$ (Compound 3) or $R^7$ and $R^1$ (Compound 2) and further attached to an acetic acid binding domain. Thus, preferred fluorescent compounds of the present invention have the formula Formula (VIII) (A)-[$(CH_2)_eC(X)NH(CH_2)_e(NHC(X)(CH_2)_e)_d]_m$—$(B)_n$; Formula (IX) (A)-$((C_6R''_4)O)_d(CH_2)_e(C(X)NH(CH_2)_e)(NH)_dC(X)NH(C_6R''_4)(CH_2)_e$—(B), wherein A is borapolyazaindacene and B is an acetic acid binding domain having Formula (I) $^-O_2CCH(R)N(CH_2CO^-_2)_2$, or formula (III) $(CH_2CO^-_2)_ZN[(CH_2)_SN(CH_2CO^-_2)]_R(CH_2)_SN(CH_2CO^-_2)_Z$.

Fluorescent compounds comprising acetic acid binding domain Formula (III) can also be used to colorimetrically detect poly-histidine affinity tag containing fusion proteins with the same sensitivity as the fluorescent signal.

The linker and non-linker substituents of the borapolyazaindacene can be present at any of $R^1$-$R^7$. The linkers may be the same or different and may be attached to the same or different binding domains. In this way a fluorescent compound may have affinity for one or more different affinity tags.

The benzofuran fluorophore has the Formula (XIV), as shown below, wherein $R^{13}$-$R^{18}$ can be any of the corresponding substituents disclosed in U.S. Pat. Nos. 4,603,209 and 4,849,362, supra. Typical non-linker substituents include hydrogen and substituted heteroaryl.

Formula (XIV)

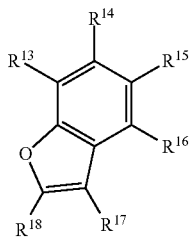

Typical fluorescent compounds comprising a benzofuran fluorophore contain a linker attached at $R^{14}$ and $R^{15}$, the compounds typically comprise two linkers, one of which is a single covalent bond at $R^{14}$ and a linker attached at the $R^{15}$ position comprising Linker Formula (VII) —(O)$_d$(CH$_2$)$_f$O(C$_6$R''$_4$)—, such a compound is demonstrated in Compound 12.

Compound 12

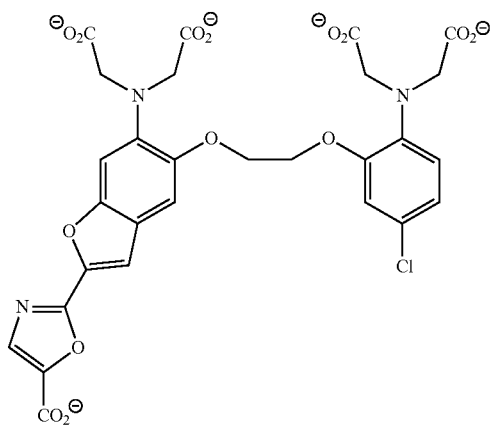

$R^{18}$ is typically substituted by a substituted heteroaryl, as Compound 12 demonstrates, preferably an oxazole. Compound 12 also demonstrates a substitution on the benzene ring (C$_6$R$_4$) of the linker; typically the ring is substituted with a halogen, preferably fluorine or chlorine.

The xanthene fluorophore has the Formula (XV), as shown below, wherein A, B and $R^{19}$-$R^{25}$ can be any of the corresponding substituents disclosed in U.S. Pat. Nos. 6,162,931; 6,130,101; 6,229,055; 6,339,392 and 5,451,343, supra. Typically, A is NR'$_2$ or OR', B is OR' or NR$_2$, wherein R' is hydrogen, an alkyl group or an acetic acid binding domain.

Formula (XV)

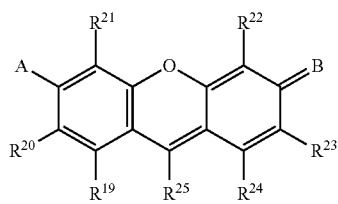

The linkers of the present invention can be present at any of the R groups and with any of the binding domains of the present invention.

When $R^{25}$ is substituted with a benzene ring (C$_6$R'$_4$), as shown below for Formula (XVI), the fluorophore is a rhodol, a rhodamine or a fluorescein depending on A and B. Rhodol fluorophores are represented when A is NH$_2$ and B is O, rhodamine fluorophores are represented when A is NH$_2$ and B is NH$_2$ and fluorescein fluorophores are represented when A is OH and B is O. These fluorohpores can be substituted by any of the corresponding substituents disclosed in U.S. Pat. Nos. 5,227,487; 5,442,045; 5,798,276; 5,846,737; 6,162,931; 6,130,101; 6,229,055; 6,339,392 and 5,451,343, supra.

Formula (XVI)

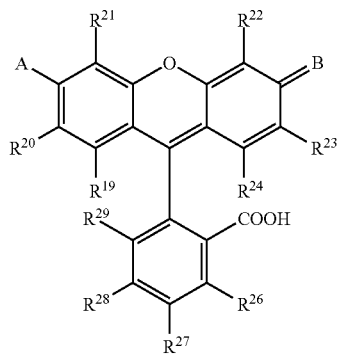

The cyanine fluorophore has the Formula (XVII), as seen below, wherein $R^{31}$-$R^{40}$ and $R^{31'}$-$R^{40'}$ can be substituted by any of the corresponding substituents disclosed in the U.S. Ser. Nos. 09/968/401 and 09/969,853 and U.S. Pat. Nos. 6,403,807; 6,348,599; 5,486,616; 5,268,486; 5,569,587; 5,569,766; 5,627,027 and 6,048,982, supra. In addition the linkers of the present invention can be substituted at any of the R groups, preferably $R^{40}$, $R^{31}$, $R^{40'}$, $R^{31'}$, $R^{39}$ and $R^{39'}$, and subsequently attached by a binding domain of the present invention.

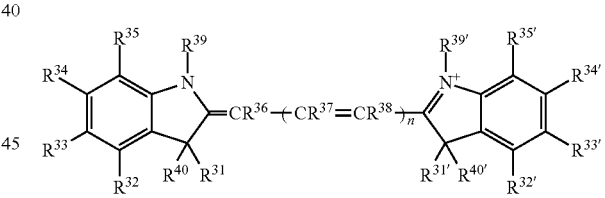

C. Methods of Use

The fluorescent compounds of the present invention may be utilized without limit for the site-specific labeling of affinity tags that results in detection of a fusion protein containing a protein of interest and an affinity tag. The methods for detecting a fusion protein containing an affinity tag include contacting a sample with a staining solution and then illuminating the sample whereby the fusion protein is detected. The staining solution comprises 1) an appropriate fluorescent compound that is capable of selectively binding, directly or indirectly, to an affinity tag and 2) a buffer.

Typically, the staining solution comprises a fluorescent compound capable of binding to poly-histidine, poly-arginine, and GST affinity tags wherein the binding domain is selected from the group consisting of glutathione, a positively charged chemical moiety and a negatively charged chemical moiety including acetic acid groups. The fluorophore is selected from the group consisting of xanthene, coumarin, cyanine, acridine, anthracene, benzofuran, indole and borapolyazaindacene. In one aspect of the present invention the staining solution for detecting fusion proteins comprising poly-histidine or poly-arginine affinity tags comprises:

a) fluorescent compound having formula A(L)m(B)n wherein A is a fluorophore, L is a linker, B is an acetic acid binding domain capable of selectively binding to a poly-histidine affinity tag, m is an integer from 1 to 4 and n is an integer from 1 to 6; and, b) a buffer having a pH about 5 to 6.9 and comprising an acceptable counter ion.

In addition, we have found that for the selective detection of poly-histidine affinity tag containing fusion proteins that the buffer preferably contains a salt and has a pKa of about 6.0 to about 7.5. Thus, preferable buffers for this application include Good's buffer, MOPS and PIPES buffers.

An example of an appropriate matching of a fluorescent compound and affinity tag is a poly-histidine affinity tag and a fluorescent compound that contains an acetic acid binding domain. The acetic acid binding domain is capable of selectively interacting with either a metal ion or the positively charged poly-histidine affinity tag.

In one aspect of the invention specific fluorescent compounds are used to detect and label fusion proteins that contain a poly-histidine affinity tag. A method of the present invention wherein the poly-histidine affinity tag containing fusion protein is detected after being separated on a polyacrylamide gel comprises the following steps:

i) immobilizing said sample on a solid or semi-solid matrix;

ii) optionally contacting said sample of step i) with a fixing solution;

iii) contacting said sample of step 1) or ii) with a staining solution comprising a buffer having a pH about 5 to 6.9 and a fluorescent compound having formula A(L)m(B)n, wherein A is a fluorophore, L is a linker, B is an acetic acid binding domain capable of selectively binding to a poly-histidine affinity tag, m is an integer from 1 to 4 and n is an integer from 1 to 6;

iv) incubating said staining solution and said sample for sufficient time to allow said compound to associate either directly or indirectly with said poly-histidine affinity tag;

v) illuminating said fluorophore with a suitable light source whereby said fusion protein is detected.

In step one (1) a sample, obtained as described below, is prepared in an appropriate buffer and immobilized on a solid or semi-solid matrix. Typically the sample is separated on a gel, typically a SDS-polyacrylamide gel. Alternatively, the sample is immobilized on solid or semi-solid matrix that includes a membrane, polymeric beads, polymeric gel, a glass surface or an array surface. When SDS-polyacrylamide gels are employed, the denaturing effects of the SDS buffer allow for the exposure of the affinity tag because when folded into a native form the affinity tag can be obscured from compounds that have affinity for the peptide. Thus, SDS gel electrophoresis facilitates the binding of the fluorescent compounds of the present invention with the poly-histidine affinity tag of a fusion protein. However, after the sample has been separated it is important that the SDS be removed from the gel with a fixing solution for maxima detection of the affinity tag because the SDS interferes with the affinity of the fluorescent compound for the affinity tag.

Therefore, the second (2) step optionally comprises incubating the gel in a fixing solution that typically includes an alcohol so as to remove the SDS before the staining solution is added to the gel. Typically, effective removal of SDS requires a step-wise contact with the fixing solution wherein the fixing solution is incubated with the gel, removed and new solution is added for an additional time period. Following the fixing step, the gel is typically rinsed with water.

During the third (3) and fourth (4) steps, the gel containing the sample, is contacted with a staining solution for a time period that permits effective non-covalent labeling of the fluorescent compound to the affinity tag. Typically this time period is from about 30 minutes to about 120 minutes. The staining solution contains a fluorescent compound that is capable of directly or indirectly binding to the affinity tag of the fusion protein and has the general formula A(L)m(B)n, as described above. For the binding of poly-histidine affinity tags, fluorescent compounds that contain an acetic acid-binding domain are preferred. Exemplified compounds 1-16 are particularly preferred. The staining solution optionally comprises an appropriate metal ion, an appropriate metal ion being one that has affinity for both the fluorescent compound and the affinity tag. As described above, some of the affinity tags have an affinity for metal ions, therefore for particular applications; a metal ion is desirable in the staining solution. The staining solution may be pre-mixed and added to the gel in one step or the individual components may be added step-wise to the gel. Preferably the gel is subjected to mild agitation while in contact with the staining solution.

During the fifth (5) step, the gel is illuminated with a suitable light source that allows for the fluorophore of the fluorescent compound affinity tag complex to be visualized whereby the fusion proteins containing a poly-histidine affinity tag is detected. Preferably, the gel is rinsed with water to remove unbound fluorescent compound prior to illumination. The suitable light source is dictated by the fluorophore of the fluorescent compound. For example, a staining solution comprising compound 1 exhibits bright-blue fluorescence (emission maximum=450 nm) when illuminated with UV-A or UV-B light from a standard ultraviolet transilluminator and compound 2 exhibits bright-green fluorescence (emission maximum=515 nm) when illuminated with visible light from a laser-based gel scanner equipped with a 470 nm second-harmonic generation (SHG) or 488 nm argon ion laser source. Typically, detection limits of poly-histidine affinity tag containing fusion proteins using staining solution containing Compound 1 or 2 is 25-65 ng in whole cell lysates.

In another aspect, the invention includes a complex of a fluorescent compound that is capable of selectively binding, directly or indirectly, to an affinity tag containing fusion protein and a fusion protein. This complex may be a ternary complex wherein a third component such as a metal ion has affinity for both the affinity tag and the fluorescent compound. Alternatively, the complex may be present without the metal ion.

1. Sample Preparation

The fusion proteins of the invention can be expressed in a number of systems including genetically engineered animals or plants, or in cells such as bacteria, yeast, insect, plant and mammalian cell cultures. The preparation of fusion proteins comprising an affinity tag can be made using standard recombinant DNA methods. Typically, a protein of interest, which is determined by the end user, is synthesized and inserted into a vector containing an affinity tag such that when inserted in frame the affinity tag and protein of interest will be translated as one fusion protein. There are many vectors that are available to one skilled in the art that contain nucleotide sequence for an affinity tag, such as pGEX (Amersham Biosciences) for GST affinity tag, pCAL (Stratagene) for calmodulin affinity tag, pFLAG (Sigma Aldrich) for FLAG affinity tag, 6× his tag vector (Qiagen) for poly-histidine affinity tag and expression vectors for Glu-Glu affinity tag including many expression systems available from Invitrogen containing vectors with a combination of affinity tags (U.S. Pat. No. 6,270,969). Alternatively, a nucleotide sequence coding for a desired affinity tag is first synthesized and then linked to a nucleotide sequence coding for the protein of interest. This fused polynucleotide is then inserted into an expression vector using techniques well known to those skilled in the art, wherein the fusion protein will be expressed when the vector is induced in a host cell such as *E. coli*. (Maniatis et al. "Molecular Cloning" (2002), Cold Spring Harbor Laboratory).

Expression systems for expressing the fusion proteins are available using *E. coli, Bacillus* sp. (Palva, I. et al., (1983) Gene 22:229-235; Mosbach, K. et al., (1983) Nature 302:543-545) Yeast and *Salmonella*. The polynucleotides encoding the fusion proteins can also be ligated to various expression vectors for use in transforming mammalian or insect cell cultures. Illustrative examples of mammalian cell lines include VERO, COS, and HeLa cells, Chinese hamster ovary (CHO) cell lines, and various cell lines available from American Type Culture Collection (Bethesda, Md.). Suitable insect cell lines include mosquito larvae, silkworm, armyworm, moth and *Drosophila* cell lines.

Expression and isolation of fusion proteins are also well known in the art (Maniatis et al, supra). Essentially, a suitable host organism is transformed with an expression vector in which the protein of interest or fused polynucleotide described above is operably linked to an expression control sequence. The transformed host cells are grown under suitable growth conditions wherein the expression vector is induced to produce fusion proteins. When the fusion protein is secreted out of the host organism the cell culture media is collected and the soluble proteins are concentrated. Alternatively, when the fusion protein is an intracellular protein the host cells are pelleted and using standard techniques the proteins are extracted wherein preferably the DNA and lipids of the cell are removed from the crude cellular extract.

When the sample is to be separated on a SDS-polyacrylamide gel the sample is first equilibrated in an appropriate buffer, such as a SDS-sample buffer containing Tris, glycerol, DTT, SDS, and bromophenol blue.

Alternatively, the constructs encoding the fusion protein of the invention are used to produce a genetically engineered animal or plant. For production of genetically engineered animals (e.g., mice, rats, guinea pigs, rabbits, and the like) the construct can be introduced into cells in vitro or in vivo. These nucleic acids can be inserted into any of a number of well-known vectors for the transfection of target cells and organisms.

After expression in the genetically engineered animal, the fusion protein is detected in a sample from the animal. The sample can be a biological fluid such as whole blood, plasma, serum, nasal secretions, sputum, saliva, urine, sweat, transdermal exudates, cerebrospinal fluid, or the like. Alternatively, the sample may be whole organs, tissue or cells from the animal. Examples of sources of such samples include muscle, eye, skin, gonads, lymph nodes, heart, brain, lung, liver, kidney, spleen, solid tumors, macrophages, mesothelium, and the like. In addition, the fusion protein may be detected intracellularly wherein a live-cell version of the present fluorescent compounds are used.

2. Staining Solution

The staining solution can be prepared in a variety of ways, which is dependent on the medium the sample is in. A particularly preferred staining solution is one that is formulated for detection of affinity tags in a gel. Specifically, the staining solution comprises a fluorescent compound of the present invention in an aqueous solution; optionally the staining solution comprises an organic solvent and a buffering component. The selection of the fluorescent compound dictates, in part, the other components of the staining solution. Any of the components of the staining solution can be added together or separately and in no particular order wherein the resulting staining solution is added to the gel. Alternatively, the components of the staining solution can be added to a gel in a step-wise fashion. The fluorescent compound is prepared by dissolving in a solvent, such as water, DMSO, DMF or methanol, usually at a final concentration of about 0.1 µM to 100 µM, preferably the fluorescent compound is present in the staining solution at a concentration of about 0.5 µM to 20 µM.

Analysis of the selectivity and specificity of the fluorescent compounds for the poly-histidine affinity tags in a SDS-polyacrylamide gel was evaluated as a function of pH. Therefore, a preferred staining solution comprises an acid to provide a moderately acidic environment for the staining reaction. An acidic environment is defined as a solution having a pH less than 6.9. Typical suitable acidic components include without limitation acetic acid, trichloroacetic acid, trifluoroacetic acid, perchloric acid, phosphoric acid, or sulfuric acid. The acidic component is typically present at a concentration of 1%-20%. The pH of the staining mixture is preferably about pH 5-6.9 and most preferred is about pH 6.5. The optimal pH for each compound used may vary slightly depending on the compound used; for compound 1, 2 and 3 pH 6.5 is preferred. Alternatively, a neutral pH is also desirable.

The pH of the staining mixture is optionally modified by the inclusion of a buffering agent in addition to or in place of an acidic component. In particular, the presence of a buffering agent has been shown to improve staining of electrophoresis gels, provided that an alcohol is included in the formulations as well. Any buffering agent that maintains a mild acidic environment and is compatible with the affinity tag and fusion protein in the sample is suitable for inclusion in the staining mixture.

Useful buffering agents include salts of formate, acetate, 2-(N-morphilino)ethanesulfonic acid, imidazole, N-2-hydroxyethyl-piperazine-N'-2-ethanesulfonic acid (PIPES), Tris (hydroxymethyl)aminomethane acetate, or Tris(hydroxymethyl)aminomethane hydrochloride, 3-(N-morpholino)propanesulfonic acid (MOPS). The family of Good's buffers, including TRIS, MES, PIPES, MOPS, are preferred for the present methods. An exemplified buffering agent is PIPES. The buffering agent is typically present in the staining mixture at a concentration of about 10 mM to 500 mM; preferably the concentration is about 25 mM to 100 mM. These buffers are particularly preferred for the non-covalent binding of a acetic acid binding domain to the poly-histidine affinity tag because they have pKa values that are similar to the pKa value of the imidazole ring of the histidine residue.

Optionally, the staining solution may include a polar organic solvent, typically an alcohol, to improve specific staining of the affinity tag. The polar organic solvent, when present, is typically included in the staining solution at a concentration of 5-50%. The presence of a polar organic solvent is particularly advantageous when staining SDS-coated proteins, as is typically the case when staining affinity tags that have been electrophoretically separated on a SDS-polyacrylamide gel. Typically, SDS is removed from a gel prior to staining by fixing, as described below, and washing, however some SDS may remain and interfere with the staining methods of the present invention. Without wishing to be bound by any theory, it appears that the presence of an alcohol improves the affinity of the fluorescent compound for the affinity tag of a fusion protein by removing any SDS that was not removed by the washing or fixing.

Optionally, the staining solution contains a metal ion salt. This is particularly useful for staining solutions used to detect poly-histidine affinity tags and calmodulin affinity tags. Nickel ions and cobalt ions have affinity for both the acetic acid binding domain of the present invention and the poly-histidine affinity tag, therefore nickel or cobalt salts are optionally included in staining solutions of the present invention. While the metal ions do not improve the selective affinity or sensitivity of the binding domain for the poly-histidine affinity tag the inclusion of the metal ions is preferable for certain applications. For this reason, a staining solution to be used to detect poly-histidine affinity tags optionally includes nickel or cobalt ions. An exemplified salt is nickel chloride but any nickel or cobalt salt known to one skilled in the art can be used. The salt is typically present in the staining solution at a concentration of about 10 nm to 1 mM; preferably the concentration is about 1 µM to 200 µM.

Alternatively, some of the compounds of the present invention, especially compounds 7-11, can be used to colorimetrically detect poly-histidine affinity tag containing fusion proteins when the staining solution comprises nickel ions at a concentration about 10 µM. Therefore, a preferred staining solution for colorimetric applications comprises nickel ions at a final concentration of about 10 µM and typically any one of compounds 7-11, See Example 19.

Calcium ions have an affinity for calmodulin, which subsequently alters the conformation of the protein such that it possesses affinity for the calmodulin affinity tag. Therefore, a staining solution specific for calmodulin contains a calcium salt along with a fluorescent compound that contains a fluorophore covalently attached to the calmodulin protein.

3. Fixing Solution

The fixing solution is required for optimal staining of poly-histidine affinity tags that have been separated and immobilized in an SDS-polyacrylamide gel. When fusion proteins are denatured and separated on a polyacrylamide gel they become coated with SDS, which masks the affinity tag such that the fluorescent compound will not specifically or selectively bind to the affinity tag. Therefore, the SDS must be removed prior to addition of the staining solution.

The fixing solution contains a polar organic solvent, typically an alcohol. Preferably, the polar organic solvent is an alcohol having 1-6 carbon atoms, or a diol or triol having 2-6 carbon atoms. Preferred alcohols are methanol or ethanol mixed with acetic acid. The alcohols are present in an aqueous solution of about 50% ethanol or methanol with 10% acetic acid. Fixing solutions containing less than 50% of ethanol or methanol generally result in incomplete removal of SDS from the gels.

To remove the SDS coat from the immobilized fusion proteins, the polyacrylamide gel is incubated in the fixing solution. Preferably the gel is fixed in multiple sequential steps, typically two. Essentially, the gel is immersed in the fixing solution for at least 20 minutes and then removed from the solution and new solution added for at least 3 hours and up to 24 hours. Generally, one step of incubating the gel in fixing solution is insufficient to remove all the SDS from the gel.

4. Illumination

At any time after staining and during the washing step, the sample is illuminated with a wavelength of light selected to give a detectable optical response, and observed with a means for detecting the optical response. Equipment that is useful for illuminating the fluorescent compounds of the present invention includes, but is not limited to, hand-held ultraviolet lamps, mercury arc lamps, xenon lamps, lasers and laser diodes. These illumination sources are optically integrated into laser scanners, fuorescences microplate readers or standard or microfluorometers. The degree and/or location of staining, compared with a standard or expected response, indicates whether and to what degree the sample possesses a given characteristic, i.e. fusion protein containing an affinity tag.

The optical response is optionally detected by visual inspection, or by use of any of the following devices: CCD camera, video camera, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

III. Kits of the Invention

Suitable kits for detecting and selectively and non-covalently labeling an affinity tag of a fusion protein also form part of the invention. Such kits can be prepared from readily available materials and reagents and can come in a variety of embodiments. The contents of the kit will depend on the design of the assay protocol or reagent for detection or measurement. All kits will contain instructions, appropriate reagents and label, and solid supports, as needed. Typically, instructions include a tangible expression describing the reagent concentration or at least one assay method parameter such as the relative amounts of reagent and sample to be added together, maintenance time periods for reagent/sample admixtures, temperature, buffer conditions and the like to allow the user to carry out any one of the methods or preparations described above.

Typically, kits useful for detecting an affinity tag of a fusion protein that has been separated on a SDS-polyacrylamide gel will include a staining solution. The kits will optionally include affinity tag containing molecular weight markers, a fixing solution and an additional detection reagent.

Typically, the affinity tag containing molecular weight markers will be stained by the fluorescent compounds of the present invention and are thus useful for estimating the size of the detected fusion protein. This enables the end user to quickly determine if a full-length fusion protein has been produced based on the estimated molecular weight. A fixing solution, as described above, is useful for removing the SDS from the polyacrylamide gel as some of the compounds of the present invention will have minimal affinity for the affinity tag in the presence of SDS. This is particularly true for the fluorescent compounds that are used for selectively binding to the poly-histidine affinity tag. Alternatively, the end user may supply the fixing solution, as this is made with reagents (alcohol) well known to one skilled in the art.

Typically, an additional detection reagent will include a total protein stain such as SYPRO® Ruby Dye and any corresponding total protein stain disclosed in U.S. Pat. No. 6,316,276. Because SDS is removed by the fixing solution prior to addition of the staining solution of the present invention, total protein stains such as SYPRO Ruby are preferred because SDS is not critical for the staining function. However, protocol changes can be made when using a total protein stain that requires SDS for staining sensitivity, such as SYPRO Orange Dye and SYPRO Red Dye, by adding SDS back to the gel prior to a total protein stain step and including SDS in the staining solution (Malone et al. Electrophoresis (2001) 22(5):919-32). A preferred solution for returning SDS back to a gel is 2% acid/0.0005% SDS, and optionally 40% ethanol, wherein the gel is incubated for at least one hour. Alternatively, the total protein stain could be preformed prior to detection of the affinity tag with the staining solution of the present invention; therefore the SDS would not need to be added back to the gel but simply removed prior to affinity tag detection as contemplated by the present invention. Therefore, alternative preferable total protein stains for gels are SYPRO Orange, SYPRO Tangerine, SYPRO Red, Coomassie Fluor dyes or any corresponding dye disclosed in U.S. Pat. Nos. 5,616,502 and 6,579,718. Alternative total protein stains for gels include Coomassie Blue or silver staining, staining techniques well known to those skilled in the art.

The staining solution of the kit will depend on (1) the affinity tag to be detected and (2) the desired absorption and emission spectra from the fluorescent compound. The choice of the binding domain dictates the particular affinity tag that will be detected. As described above, particular binding domains of the present invention have affinity for poly-histidine affinity tag, poly-arginine affinity tag, GST affinity tag and calmodulin affinity tag. The absorption and emission spectra of the fluorescent compound is dictated by the fluorophore. The fluorophores of the present invention cover almost the entire spectrum of UV light, including the popular wavelengths 488, 532 and 633. Particularly useful fluorophores in fluorescent compounds for detecting poly-histidine affinity tags are coumarin, benzofuran, borapolyazaindacene, cyanine and xanthenes. Another important aspect of the staining solution is the pH and the pKa value wherein the optimal pH is dependent on the fluorescent compound in the staining solution and the pKa value is dependent on the affinity tag. Typically, a staining solution for detecting poly-histidine affinity tags is mildly acidic or neutral, pH 5 to 7, and has a pKa of about 6.0 to about 7.5. Preferred is a pH about 6.5 and a pKa of about 6.8.

It is understood by one skilled in the art, that any of the fluorescent compounds contemplated by the present invention can be used to in a staining solution to be included in a kit. The compounds are not intended to be limited to only the described preferred embodiments.

IV. Applications

The compounds and methods described above for the site-specific labeling of affinity tags has many applications and is not simply limited to detection of affinity tags on a solid or semi-solid matrix. One skilled in the art will appreciate many other applications the fluorescent compound of the present invention can be used in. For example, the fluorescent compounds may be used to label affinity tag containing fusion protein in a solution. This would serve the purpose for a quick determination for the presence of the desired fusion protein or for more involved applications wherein the fluorescent compound functions as a tracer of the fusion protein in an in vitro assay. Such assays may involve, but are not limited to, the study of protein-protein interaction, signal transduction, post-translational modifications, monitoring, metabolism and cell trafficking.

One skilled in the art will also recognize that live cell (cell permeant) versions of the fluorescent compounds could be used in a wide range of in vivo assays. Affinity tag containing fusion proteins could be produced in an appropriate host cell, eukaryotic or prokaryotic, and the fluorescent compounds of the present invention could site-specifically label the intracellular fusion proteins providing for a rigorous analysis of a protein of interest. One could envision that this would be applicable for determining drug targets or studying the functional proteome.

In one embodiment, modification of carboxylic groups with acetoxymethyl (AM) ester groups results in uncharged molecules than can penetrate cell membranes. Once inside the cells, the lipophilic blocking groups are cleaved by non-specific esterases revealing a binding domain of the present invention, e.g., acetic acid binding domain.

By way of example, the following present compound (Compound 13) has been derivatized to comprise three AM ester groups.

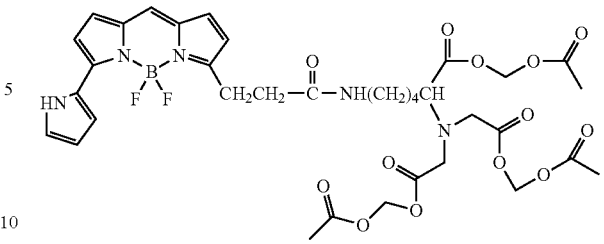

When the compound enters a cell the AM ester groups will be cleaved revealing an acetic acid binding domain according to the following structure (Compound 14).

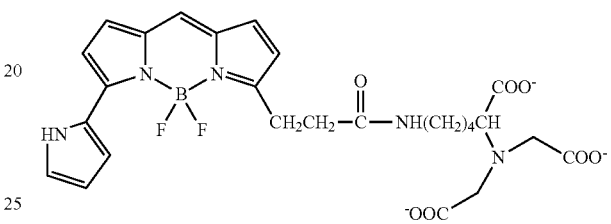

Thus, the present compounds that comprise acetic acid binding domains can be represent by the formula —N(CH$_2$COOR$^{30}$) wherein R$^{30}$ is the same or different and is selected from the group consisting of hydrogen, salt ions, an electron pair and —CH$_2$OCOCH$_3$ (AM ester). In this way the compounds of the present invention represent both cell permeant and cell impermeant versions wherein for the live cell versions the AM ester is cleaved unmasking the acetic acid binding domain.

Fluorogenic versions of the fluorescent compounds, i.e., version that demonstrate a detectable change upon non-covalently binding to an affinity tag or compounds that are essentially non-fluorescent until bound to an affinity tag, could be used in certain applications. For example, the fluorogenic compounds could be attached to a solid or semi-solid matrix and when an aliquot of a sample thought to contain an affinity tag was added a change in the detectable response would indicate the presence of an affinity tag. Such solid or semi-solid matrix include without limitation, multiwell plastic microplates, glass slides and arrays.

Additionally, some of the fluorescent compounds are also colorimetric, especially compounds 7-10. These compounds can be used in the same applications as the non-colorimetric compounds however these compounds are especially useful for detecting affinity tags in SDS-polyacrylamide gels and membrane blots. The use of the colorimetric fluorescent compounds can be equally as sensitive as detection by fluorescent wavelength and do not require any special equipment for visualizing. The gels incubated with the compounds can be inspected as one would with a Coomassie brilliant blue stained gel to determine the presence of an affinity tag containing fusion protein. (See, Example 19)

A detailed description of the invention having been provided above, the following examples are given for the purpose of illustrating the invention and shall not be construed as being a limitation on the scope of the invention or claims.

EXAMPLES

Example 1

Synthesis of compound 1 [7-amino-3-(1-carboxy-1-(bis(carboxymethyl)amino)-5-(acetylamino))pentyl-4-methylcoumarin-6-sulfonic acid, tetratriethylammonium salt]

To a solution of 7-amino-3-((((succinimidyl)oxy)carbonyl)methyl)-4-methylcoumarin-6-sulfonic acid (48 mg, 0.11 mmol) in DMF (3 mL) is added a solution of NTA (34 mg, 0.13 mmol) and triethylamine (0.1 mL) in water (1 mL). The mixture is stirred at room temperature for 15 minutes and then concentrated to dryness in vacuo. The crude product is purified on SEPHADEX LH-20, eluting with water to give pure Compound 1 (59.3 mg).

Compound 1

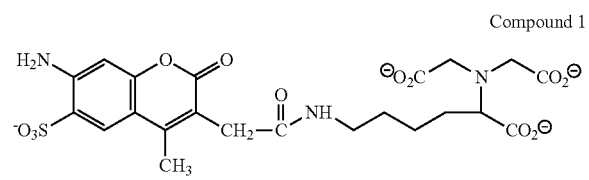

Example 2

Synthesis of Compound 2 [4,4-difluoro-4-bora-3a,4a-diaza-s-indacene-3,5-bis((6-(propionyl)amino-2-bis(carboxymethyl)amino)hexanoic acid), hexatriethylammonium salt]

To a solution of 4,4-difluoro-4-bora-3a,4a-diaza-s-indacene-3,5-dipropionic acid (86 mg, 0.26 mmol) in DMF (2 mL) at 10° C. is added O-succinimidyl-N,N,N',N'-tetramethyluronium tetrafluoroborate (170 mg, 0.56 mmol) and triethylamine (0.087 mL). The mixture is stirred at 10° C. for 15 minutes and then followed by the addition of a solution of NTA (160 mg, 0.61 mmol) and triethylamine (0.4 mL) in water (2 mL). The mixture is stirred at 10° C. for another 30 minutes and then concentrated to dryness in vacuo. The residue is purified on SEPHADEX LH-20 to give compound 2 (50 mg).

Compound 2

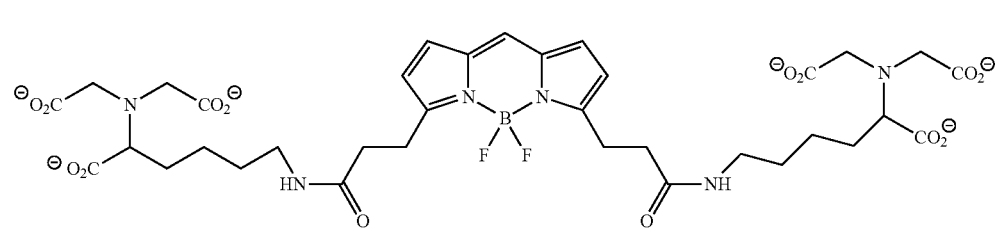

Example 2A

Synthesis of Compound 3

Compound 3 is synthesized similar to Compound 2 but with the starting material 4,4-difluoro-1,3,5,7-tetramethyl-4-bora-3a,4a-diaza-s-indacene-2,6-dipropionic acid.

Compound 3

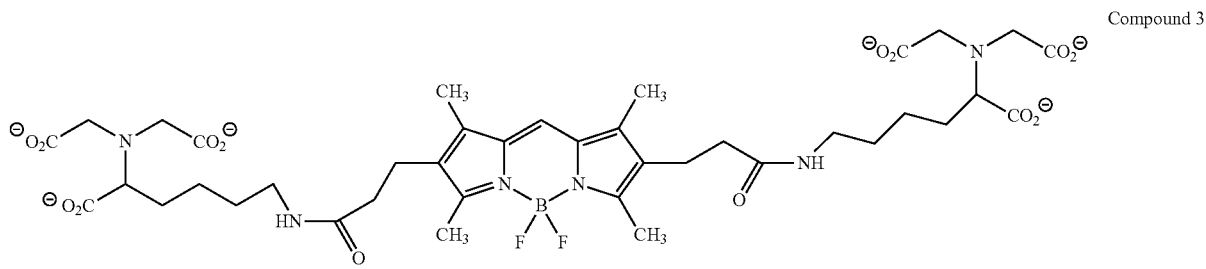

Example 3

Synthesis of Compound 4 [7-Hydroxy-6,8-difluoro-3-(1-carboxy-1-(bis(carboxymethyl)amino)-5-(acetylamino))pentyl-4-methylcoumarin, triethylammonium salt]

To a solution of 7-hydroxy-6,8-difluoro-4-methylcoumarin-3-acetic acid, succinimidyl ester (44 mg, 0.12 mmol) in DMF (3 mL) is added a solution of NTA (34.5 mg, 0.13 mmol) and triethylamine (0.1 mL) in water (1 mL). The solution is stirred at room temperature for 30 minutes and then concentrated to dryness in vacuo. The residue is purified on SEPHADEX LH-20 to give compound 4 (40.9 mg).

Compound 4

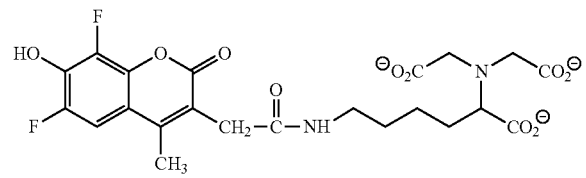

Example 4

Synthesis of Compound 5 [7-Hydroxy-3-(1-carboxy-1-(bis(carboxymethyl)amino)-5-(acetylamino))pentyl-4-methylcoumarin]

To a solution of 7-hydroxy-4-methylcoumarin-3-acetic acid, succinimidyl ester (141 mg, 0.427 mmol) in THF (5 mL) is added a solution of NTA (74 mg, 0.282 mmol) and sodium bicarbonate (135 mg, 1.6 mmol) in water (5 mL). The mixture is stirred at room temperature for 15 minutes and then acidified to pH=4 with 0.1 M HCl. The solution is concentrated to dryness in vacuo and the residue is purified on SEPHADEX LH-20, eluting with MeOH:water (1:1) to give compound 5 (55 mg).

Compound 5

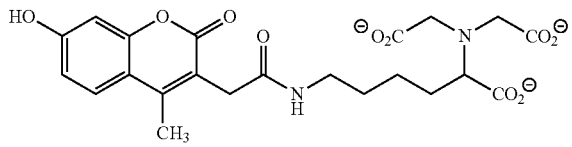

Example 5

Synthesis of compound 6 [7-dimethylamino-4-(1-carboxy-1-(bis(carboxymethyl)amino)-5-(acetylamino))pentylcoumarin, trisodium salt]

To a solution of 7-dimethylaminocoumarin-4-acetic acid, succinimidyl ester (100 mg, 0.29 mmol) (1.5 mL) is added a solution of NTA (38 mg, 0.145 mmol) and sodium bicarbonate (61 mg, 0.725 mmol) in water (1.5 mL). The mixture is stirred at room temperature for 15 minutes and then concentrated to dryness in vacuo. The residue is purified on SEPHADEX LH-20, eluting with methanol:water (1:1) to give compound 6.

Compound 6

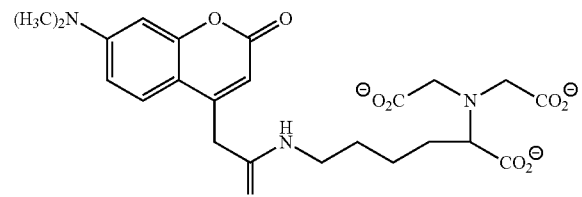

Example 6

Synthesis of Compound 7

To a solution of 4,4-difluoro-5,7-dimethyl-4-bora-3a,4a-diaza-s-indacene-3-propionyl ethylenediamine, hydrochloride (BODIPY® FL EDA, Molecular Probes 2390, 20 mg, 0.054 mmol) in 3 mL dry DMF under argon is added DIEA (9 µL, 0.054 mmol), followed by solid DTPA anhydride (Aldrich, 77 mg, 0.22 mmol). The resulting orange mixture is stirred at room temperature for 2 hours and then diluted with 5 mL water. The pH is raised to 9.0 with aqueous KOH. After another 2 hours, the reaction solution is concentrated in vacuo and the product purified by column chromatography on Sephadex LH-20 using E-pure water as eluant to give compound 7 as 22 mg of orange powder.

Compound 7

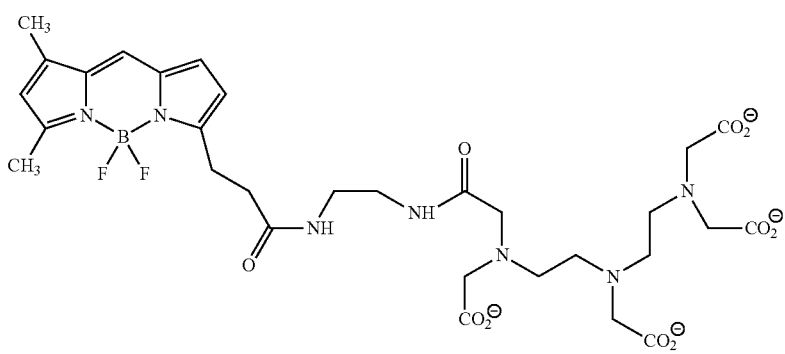

Example 7

Synthesis of Compound 8

4,4-difluoro-5,7-dimethyl-4-bora-3a,4a-diaza-s-indacene-3-propionyl ethylenediamine, hydrochloride (BODIPY® FL EDA, Molecular Probes 2390, 7 mg, 0.019 mmol) is dissolved into a mixture of (S)-1-p-isothiocyanatobenzyldiethylenetriaminepentaacetic acid (DTPA isothiocyanate, Molecular Probes 24221, 10 mg, 0.019 mmol) in 2 mL water. The pH (~3) is raised to 10 with aqueous sodium carbonate. The resulting orange solution is stirred at room temperature for 3.5 hours, then concentrated in vacuo. The residue is purifed by column chromatography on Sephadex LH-20 using E-pure water as eluant to give compound 8 as 29 mg of orange powder.

is washed with 10% HCl (2×30 mL), water (30 mL), brine (30 mL) and dried over sodium sulfate. The solution is concentrated and put on a silica gel column (packed with ethyl acetate). The column is eluted first with ethyl acetate to remove impurities and then the desired product is eluted with 10:1 chloroform-methanol. Pure fractions are combined and the solvent evaporated to give amide 9a (0.54 g, 54%) as a viscous oil.

For the synthesis of aminoacid 9b, the carbamate 9a (0.700 g, 0.683 mmol) is dissolved in 10 mL of TFA. The reaction mixture is kept for 3 days at room temperature. Volatiles are evaporated in vacuo and the residue is re-evaporated twice from toluene, leaving a viscous oil. The oil is stirred with ethyl acetate until it solidifies. The resulting solid is filtered and dried in vacuum to give the aminoacid 9b (0.400 g, 96%).

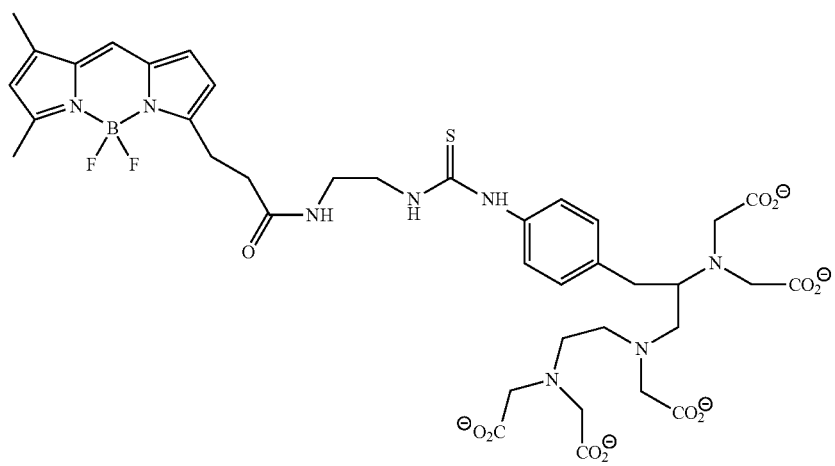

Compound 8

Example 8

Synthesis of Compound 9

For the synthesis of carbamate 9a a solution of penta-t-butyl 1-(S)-(p-aminobenzyl)-diethylenetriamine-pentaacetate (prepared according to the published procedure of Donald T. Corson & Claude F. Meares. *Bioconjugate Chem.*, 11(2), 2000, 292-299, 0.800 g, 1.03 mmol) in 20 mL of methylene chloride is added 1 mL of pyridine followed by the addition of a solution of the acid chloride of N—CBZ-6-aminohexanoic acid (0.290 g, 1.02 mmol) in 5 mL of methylene chloride. The reaction mixture is stirred overnight at room temperature and concentrated in vacuo. The residue is dissolved in 100 mL of ethyl acetate and the resulting solution For the synthesis of compound 9, the aminoacid 9b (0.090 g, 0.147 mmol) is suspended in 10 mL of water. The pH is adjusted to pH~8 using 1M KOH. The resulting solution is added to a solution of 6-((4,4-difluoro-1,3-dimethyl-5-(4-methoxyphenyl)-4-bora-3a,4a-diaza-s-indacene-2-propionyl)amino)hexanoic acid, succinimidyl ester (BODIPY® TMR-X, SE, MPI 6117, 0.03 g, 0.049 mmol) in 5 mL of DMF. The reaction mixture is stirred overnight at room temperature. The pH is monitored and adjusted to pH~8 during the first 2 hrs. The volatiles are removed in vacuo. The residue is re-dissolved in water and put onto a Sephadex LH-20 column. The column is eluted with E-pure water. Pure fractions containing the most polar fluorescent product are combined. The resulting solution is concentrated to ~3 mL in vacuo and then lyophilized to give Compound 9 as a red powder (0.061 g).

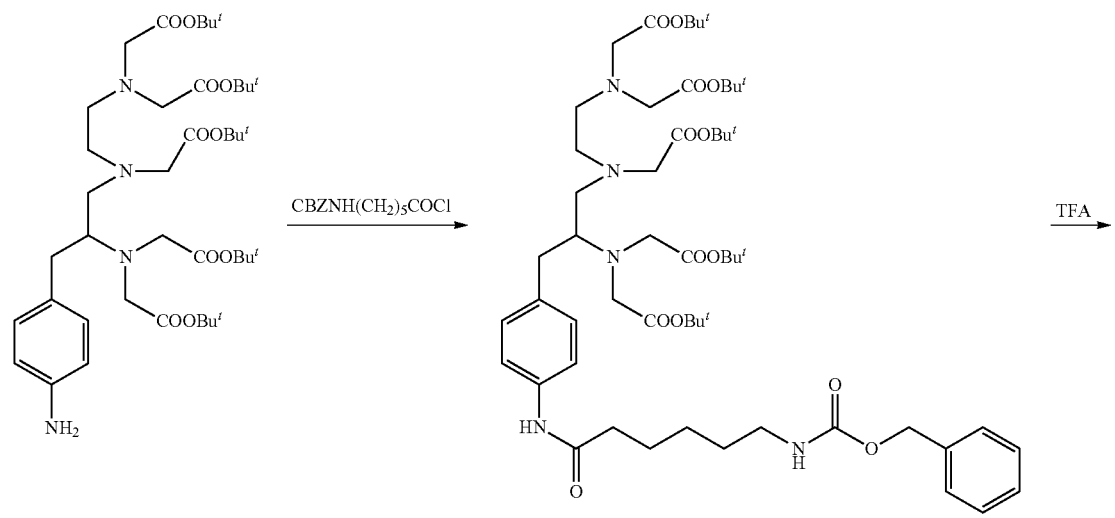
9a
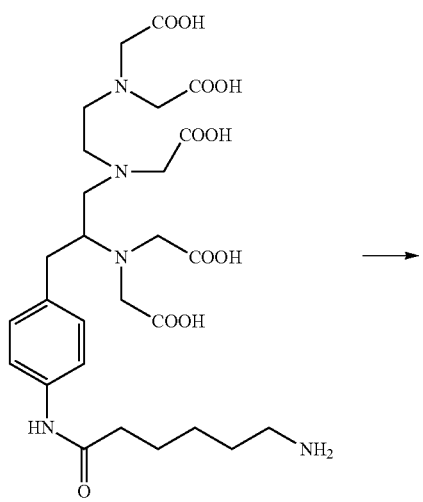
9b
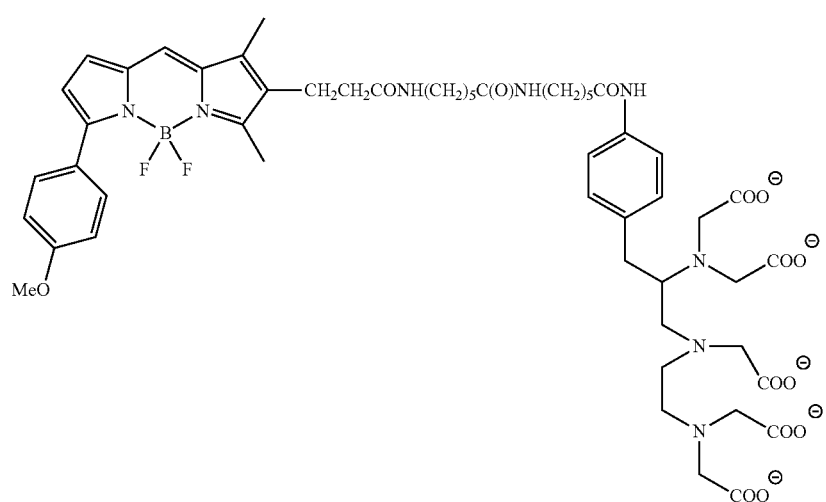
Compound 9

Example 9

Synthesis of Compound 10

5-(((4-(4,4-difluoro-5-(2-thienyl)-4-bora-3a,4a-diaza-s-indacene-3-yl)phenoxy)acetyl)amino)pentylamine, hydrochloride (BODIPY® TR cadaverine, Molecular Probes 6251, 10 mg, 0.019 mmol) is dissolved into a mixture of (S)-1-p-isothiocyanatobenzyldiethylenetriaminepentaacetic acid (DTPA isothiocyanate, Molecular Probes 24221, 10 mg, 0.019 mmol) in 2 mL water. The pH (~2) is raised to 10 with aqueous sodium carbonate. The resulting blue solution is stirred at room temperature for two days, then concentrated in vacuo. The residue is purifed by column chromatography on Sephadex LH-20 using E-pure water as eluant to give compound 10 as 2 mg of purple powder.

Example 10

Synthesis of BODIPY FL-TTHA Compound 11

To a solution of 4,4-difluoro-5,7-dimethyl-4-bora-3a,4a-diaza-s-indacene-3-propionyl ethylenediamine, hydrochloride (BODIPY® FL EDA, Molecular Probes 2390, 20 mg, 0.054 mmol) in 3 mL dry DMF under argon is added DIEA (9 µL, 0.054 mmol), followed by solid TTHA anhydride (prepared according to Achour et al., *Inorganic Chemistry* 1998, 37: 2729-2740, 100 mg, 0.22 mmol). The resulting orange mixture is stirred at room temperature for 2 hours, then diluted with 5 mL water. The pH is raised to 9.0 with aqueous KOH. After another 2 hours, the reaction solution is concentrated in vacuo and the product purified by column chromatography on Sephadex LH-20 using E-pure water as eluant to give compound 11 as an orange powder.

Example 11

Synthesis of Compound 13

Nα,Nα-Bis(carboxymethyl)lysine (0.157 g, 0.600 mmol) was dissolved in a mixture of 4.8 mL 1M $Et_3NH_2CO_3$ buffer and 15 mL water. 4,4-Difluoro-5-(2-pyrrolyl)-4-bora-3a,4a-diaza-s-indacene-3-propionic acid, succinimidyl ester (BODIPY® 576/589 SE, 0.170 g, 0.401 mmol) was dissolved in 30 mL of dioxane and added to the amino acid solution. The reaction mixture was stirred for 1 h at RT and evaporated to dryness. The residue was re-evaporated from water to remove tetraethylammonium salts. The crude product was dissolved Compound 10

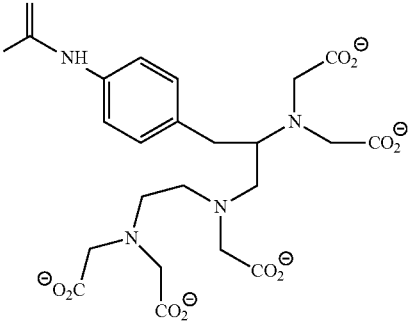

in water and loaded onto an LH-20 column (packed in water). The column was eluted with water. Fractions containing pure material were combined and lyophilized to give compound 13 as a dark red powder (0.120 g, 34%) as its triethylammonium salt.

Example 12

Synthesis of Compound 14

The triethylammonium salt 13 (0.120 g, 0.137 mmol) was suspended in 5 mL of DMF. i-$Pr_2NEt$ (0.14 mL, 0.82 mmol) was added to the suspension followed by $BrCH_2OAc$ (0.08

Compound 11

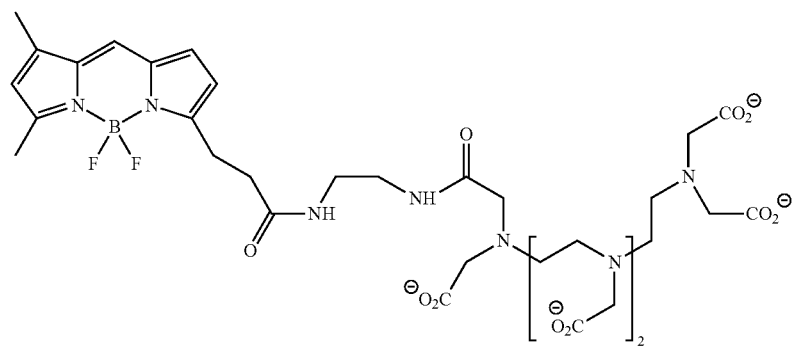

mL, 0.8 mmol). The reaction mixture was stirred for 4 hrs at RT and then diluted with brine (30 mL). The product was extracted with ethyl acetate (3×30 mL). The combined extracts were washed with water (3×30 mL), brine (30 mL), dried over anhydrous sodium sulfate and evaporated. The crude product was dissolved in chloroform and loaded onto a silica gel column packed with 4:8:0.1 chloroform-ethyl acetate-acetic acid. The same solvent mixture was used to elute the column. Fractions containing pure product were combined and evaporated in vacuo. The residue was re-evaporated from toluene to give AM ester 14 as a dark purple wax (0.081 g, 75%).

Example 13

Synthesis of Compound 15 p-Nitrophenylalanine methyl ester hydrochloride 15a (Bachem, cat. #F-1910; 2.00 g, 7.68 mmol) was added portionwise to 9.9 mL (92 mmol) of diethylenetriamine with stirring at RT. When all hydrochloride was added the mixture was stirred for additional 5 hrs at RT. Excess of diethylenetriamine was removed in vacuum. The residue was dissolved in 20 mL of conc. ammonia solution and the product was extracted with $CH_2Cl_2$ (10×20 mL). The combined extracts were dried over sodium sulfate and concentrated in vacuum to give amide 15b (1.98 g, 87%) as yellow oil.

Amide 15b (1.98 g, 6.71 mmol) was dissolved in 60 mL of dry THF. $BH_3$.THF complex (1 M solution of in THF, 60.4 mL, 60.4 mmol) was added to amide 15b dropwise under nitrogen with stirring and cooling (ice/water bath). After all amount of complex was added, the temperature was allowed to rise to ambient and the mixture was stirred under reflux for 15 hrs. Then the mixture was cooled again (ice/water bath) and excess of $BH_3$ was carefully decomposed with water (5 mL, dropwise, stirring). The resilting solution was concentrated in vacuum and the residue mixed with 35 mL of water and 35 mL of conc. HCl. The solution was stirred for 3.5 hrs under reflux then 20 hrs at RT and evaporated to dryness. The residue was mixed with 50 mL of conc. ammonia and 50 mL of water. The product was extracted with chloroform (6×100 mL). The combined extracts were dried over $Na_2SO_4$ and evaporated to give amine 15c (1.37 g, 73%) as yellow oil.

Amine 15c (1.37 g, 4.88 mmol) was dissolved in 50 mL of DMF. Diisopropyethylamine (12.7 mL, 72.9 mmol) and tert-butyl bromoacetate (8.64 mL, 58.5 mmol) were added to the solution, followed by addition of powdered KI (0.89 g, 5.4 mmol). The reaction mixture was stirred for 72 hrs at RT and evaporated to dryness. The residue was mixed with 100 mL of water and the product extracted with diethyl ether (3×40 mL). The combined extracts were washed with water (40 mL), brine (40 mL), dried over sodium sulfate and evaporated. The crude product was dissolved in 2:1 hexanes-ethyl acetate mixture and loaded on silica gel column (packed with 2:1 hexanes-ethyl acetate mixture). The same solvent mixture was used to elute the column. Pure fractions were combined and evaporated to give hexaester 15d as yellow oil (1.68 g, 36%).

Ester 15d (1.68 g, 1.74 mmol) was dissolved in 50 mL of methylene chloride. 10% Pd/C (100 mg) was added to the solution and the mixture was shaken in Parr Apparatus at 50 psi for 4 hrs. The catalyst was filtered off, and the solution was concentrated in vacuum. The residue was dissolved in 9:1 $CH_3CN$:water mixture and the solution was loaded on silica gel column (packed with 9:1 $CH_3CN$:water mixture). The column was eluted with the same solvent mixture. Pure fractions were combined and concentrated in vacuum to give amine 15e as yellow oil (1.54 g, 95%).

N—CBZ-6-aminohexanoic acid 15f (0.600 g, 2.26 mmol) was dissolved in 5 mL of methylene chloride. DCC (0.234 g, 1.13 mmol) was added to the solution and reaction mixture was stirred over weekend at RT. The precipitate was filtered off and washed with 2 mL of methylene chloride. Methylene chloride solutions were combined and evaporated to give anhydride 15g (0.58 g, quant.).

Amine 15e (0.600 g, 0.640 mmol) was dissolved in 5 mL of DMF. i-$Pr_2$NEt (0.54 mL, 3.1 mmol) was added to the solution followed by addition of anhydride 15g (0.58 g, 1.13 mmol) as a solution in 3 mL of DMF. The reaction mixture was stirred overnight at RT. The solution was diluted with 80 mL of 0.5M KOH and the product was extracted with EtOAc (3×40 mL). The combined extracts were washed with water (3×30 mL), brine (30 mL), dried over sodium sulfate and evaporated. The crude product was suspended in 1:1 hexanes-EtOAc mixture and loaded on silica gel column (packed with 2:1 EtOAc-hexanes mixture. The column was eluted first with 2:1 EtOAc-hexanes mixture and then with 10% MeOH in chloroform. Fractions containing pure amide were combined and evaporated to give desired amide 15h as viscous oil (0.846 g).

CBZ protected amide 15h (0.84 g, 0.71 mmol) was dissolved in 5 mL of TFA. The solution was kept at RT for 72 hrs, and then evaporated in vacuum. The residue was re-evaporated from toluene (3×20 ML) and triturated with EtOAc. White precipitate formed. Mixture was centrifuged, supernatant separated and solid washed with fresh EtOAc. Mixture was stirred and centrifuged again. After supernatant was removed the procedure was repeated three more times and then the product was dried in vacuum to give amine 15i as a white solid (0.521 g, 89%).

Amine 15i (0.054 g, 0.065 mmol) was dissolved in 4 mL of DMF. i-$Pr_2$NEt (0.023 mL, 0.13 mmol) was added to the solution. White precipitate formed. Water was added to the solution (about 2 mL) until all solid dissolved. SE ester D6117 (0.02 g, 0.033 mmol) was dissolved in 2 mL of DMF and two solutions were mixed. After stirring for 20 min. 0.5 g of sodium bicarbonate was added to the solution and the reaction mixture was stirred for 48 hrs at RT. Reaction mixture was concentrated in vacuum, the residue dissolved in water (4 mL) and loaded on LH-20 column. The column was eluted with water. Fractions containing most polar fluorescent product were combined and concentrated to the volume ~10 mL. Solution was acidified with 1 mL of 10% HCl and the product was extracted with n-BuOH (3×10 mL). The combined extracts were concentrated in vacuum and the residue was mixed with 10 mL of water. The solid was filtered off, washed with water (2 mL) and dissolved in 5% ammonia (~2 mL). The resulting solution was loaded on LH-20 column ant eluted with water. Pure fractions were combined concentrated in vacuum and lyophilized to give amide 15 (0.014 g of Compound 15, isomer a and 0.022 g of Compound 15, isomer b. Both fraction show similar purity by LCMS). MS+H: 1257 (calculated for $C_{58}H_{78}N_9O_{16}BF_2 \cdot 3NH_3$: 1256).

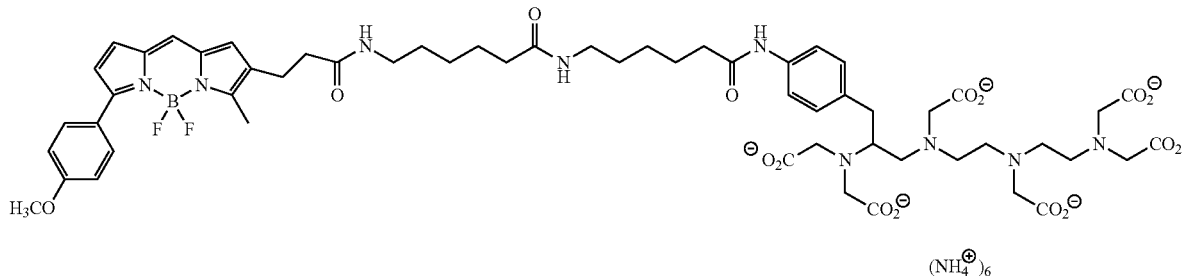

Compound 15

Example 14

Synthesis of Compound 16

NTA (0.100 g, 0.382 mmol) was dissolved in 2 mL of water. The pH of the solution was adjusted to 8 using 1M KOH. (D6117, Molecular Probes, Inc.) (0.100 g, 0.164 mmol) was dissolved in 2 mL of DMF and added to solution of amino acid. The reaction mixture was stirred for 2 hrs at RT. During the reaction pH was monitored and adjusted to 8 with 1M KOH. After all SE ester (D6117) was consumed the reaction mixture was evaporated. The residue was dissolved in water and solution was loaded on LH-20 column. The column was eluted with water. Fractions containing pure product (TLC, A/B 1:1) were combined, concentrated to the volume of 2-3 mL, and lyophilized to give Compound 16 (0.130 g, 91%). [MS–H] 754.3, calculated for $C_{37}H_{48}N_5O_9BF_2$ 755.6. Solution A: dioaxane:i-PrOH:water:ammonia 80:40:68:72. Solution B: dioaxane:i-PrOH:water:ammonia 15:58:13:14 was transferred to 50 ml of fresh LB medium containing 0.1 mg/ml ampicillin and grown until they reached an optical density at 595 nm ($OD_{595}$) of 0.8. At this point 5 ml of culture was removed and immediately frozen on dry ice. To the rest of the culture 0.8 mM IPTG was added to induce the overexpression of the subunits. Samples (5 ml each) were taken after 10 min, 30 min, 1 h, 1.5 h, 2 h, 2.5 h, and 3 h and again frozen on dry ice.

The cells from the different time points were pelleted (at 5000×g) and the supernatant was discarded. The cells were lysed adding 200 µl of buffer I (0.3% SDS, 200 mM DTT, 28 mM Tris base, 28 mM Tris HCl, pH 8.0) and incubated for 10 min, followed by a short (2 min) sonication to break the cells open completely. To remove the DNA, 20 µl of buffer II (24 mM Tris Base, 476 mM Tris HCl, 50 mM $MgCl_2$, 1 mg/ml DNAse I, 0.25 mg/ml RNAse A) was added and the cell extract was incubated for another 10 min. Finally, 100 µl of the cell extract was removed and mixed with 40 µl of 5×SDS sample buffer (290 mM Tris, 25 glycerol, 250 mM DTT, 10% SDS, 0.01% bromophenol blue). After vortex mixing, the

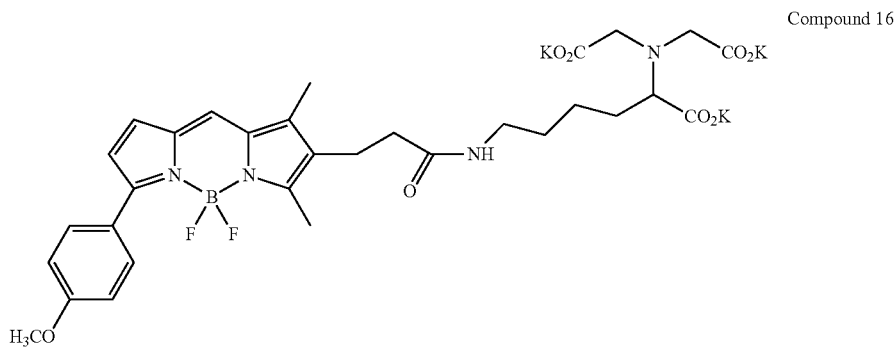

Compound 16

Example 15

Detection of Fusion Proteins Containing a Poly-Histidine Affinity Tag in Polyacrylamide Gels

*Escherichia coli* BL21 DE3 cells were transformed with plasmids containing either the human ATP synthase a subunit, the d subunit (including the leader sequence) or urate oxidase. Both proteins were constructed to have a poly-histidine affinity tag comprising six histidine residues, at the N-terminus and could be induced by isopropyl-beta-D-thiogalactoside (IPTG) addition to the medium. Pre-cultures (10 ml) were grown overnight in bacterial cell culture medium (LB medium) at 37° C. with constant shaking. The next day 100 µl samples were centrifuged at maximum speed (~12,000×g) in a microcentrifuge and the supernatant was subjected to SDS-polyacrylamide gel electrophoresis.

Proteins were separated by SDS-polyacrylamide gel electrophoresis utilizing 13% T, 2.6% C gels. % T is the total monomer concentration expressed in grams per 100 ml and % C is the percentage crosslinker. The 0.75 mm thick, 6×10 cm gels were subjected to electrophoresis using the Bio-Rad mini-Protean III system according to standard procedures.

Following separation of the proteins on a SDS-polyacrylamide gel, the gels were fixed for 20 minutes in 100 ml of 50% ethanol/7% acetic acid and then fixed overnight in 100 ml of fresh fixative solution to ensure complete elimination of SDS. Gels were next washed 3 times for 20 minutes each in deionized water. The gels were then incubated in a staining solution containing 10 μM compound 1 or 2 μM compound 2; 100 μM NiCl$_2$; 50 mM PIPES at pH 6.5 for 45-90 minutes in a total volume of 25 ml. Afterwards, the gels were washed 2 to 4 times for 20 minutes each in deionized water. In order to ensure that the optimal signal was documented, gels were imaged after the second and fourth wash.

The resulting blue-fluorescent signal produced by compound 1 was visualized using 300 nm trans-illumination and 520 nm band pass emission filter on the Lumi-Imager (Roche Biochemicals, Indianapolis, Ind.), a cooled CCD-camera based system digitizing at 1024×1024 pixels resolution with 16-bit gray scale levels assigned per pixel. Alternatively, the signal was visualized utilizing a UVP transilluminator/Polaroid MP4+ camera system (UVP, Upland, Calif.) with 365 nm transillumination and photographed with Polaroid 667 black-and-white print film using a SYPRO® protein gel stain photographic filter (Molecular Probes, Eugene, Oreg.).

The resulting green-fluorescent signal produced by compound 2 was visualized using the 473 nm excitation line of the SHG laser on the Fuji FLA-3000G Fluorescence Image Analyzer (Fuji Photo, Tokyo, Japan) with the 520 nm long pass filter or the 580 nm band pass filter, respectively. See, FIGS. 1 and 2.

Example 16

Detection of Fusion Proteins Containing a Poly-Histidine Affinity Tag in Polyacrylamide Gels that are First Separated by Isoelectric Focusing E. coli cultures of induced and un-induced human ATP synthase d subunit (100 ml each) were grown as described in Example 11 and the cells were pelleted at 5000×g. The cells were resuspended in 2 ml of 25 mM Tris, pH 7.5 before addition of 4 ml of 28 mM Tris base, 22 mM Tris HCl, 0.3% SDS to lyse the cells. After 5 minutes, a sufficient amount of 1 M MgCl$_2$ was added to make a final concentration of 5 mM, followed by 10 μl RNAse A (10 mg/ml) and 40 μl DNAse 1 (10 mg/ml) to digest the nucleic acids. The raw cell extract was then mixed with 6 ml Urea buffer (7 M Urea, 2 M Thiourea, 2% Chaps, 1% Zwittergent 3-10, 65 mM DTT) and insoluble material was pelleted by centrifigation (15,000×g, SS34 rotor). The supernatant was then injected into the Rotofor chamber (Bio-Rad Laboratories, Hercules, Calif.) according to the manufacturers manual using the same urea buffer in the chamber. The proteins were focused for roughly 3 h before harvesting into 20 fractions spanning a pH range of 2-12. Fractions were collected using the system's vacuum manifold and were acetone-precipitated and resuspended in SDS-sample buffer. For SDS polyacrylamide gel electrophoresis 30 μl of sample per fraction was utilized and gels were subsequently stained for the presence of the oligopoly-histidine affinity tag using Compound 2 as described in Example 11.

Example 17

Serial Dichromatic Detection of Poly-Histidine Affinity Tag and Total Protein in SDS-Polyacrylamide Gels Following selective staining of the poly-histidine affinity tag containing fusion proteins separated on a SDS-polyacrylamide gel, as described in Example 15, the gel was incubated overnight with SYPRO® Ruby protein gel stain with gentle orbital shaking, typically 50 rpm. The gel was then incubated in 7% acetic acid, 10% methanol for 30 minutes, also at 50 rpm. The fluorescent signal from the affinity tag containing proteins and non-affinity tag proteins was collected with a standard CCD camera-based imaging system with 300 nm UV light excitation and a 600 nm bandpass filter.

Example 18

Detection of Poly-Histidine Affinity Tag Containing Fusion Proteins in Two-Dimensional Polyacrylamide Gels E. coli BL21 DE 3 cells expressing poly-histidine affinity tag ATP synthase d subunit induced with IPTG were prepared and a lystate (100 μl) was diluted in urea buffer (2 M Thiourea, 7 M Urea, 2% CHAPS, 1% Zwittergent 3-10, 0.8% Ampholytes 3-10, 56 mM DTT) and applied on a first dimension IPG strip (3-10 non linear, 18 cm; Amersham Pharmacia) that had been rehydrated overnight in urea buffer. The strips were overlayed with 2 ml of light mineral oil and the proteins focused for 24.5 h, at 70 kVh and 20° C. for a final voltage of 100 μA/strip. The IPG strips were equilibrated in 300 mM Tris/Base, 75 mM Tris/HCl, 3% SDS, 50 mM DTT, 0.01% Bromophenol Blue for 10 min and then laid on top of a 12.5% SDS-polyacrylamide gel. Electrophoresis was performed according to standard procedures for 4.5 h.

After the second dimension electrophoresis the gels were fixed in 10% ethanol, 7% acetic acid overnight to remove SDS. The next day the gels were washed twice with dH$_2$O for 20 minutes each before equilibration in 50 mM PIPES, 1 mM NiCl$_2$, pH 6.5. The gels were washed again twice for 15 minutes each before staining with 10 μM Compound 1 in 50 mM PIPES, pH 6.5 (250 ml). To remove excess dye the gels were washed twice in dH2O for 20 minutes each. The staining was imaged on a Lumi-Imager (Roche) using UV light excitation and a 520 nm emission filter with a 5 s exposure time.

Following detection of poly-histidine affinity tag containing fusion proteins, the gels was stained for total protein using SYPRO® Ruby protein gels stain as described in Example 17.

Example 19

Detection of Fusion Proteins Containing a Poly-Histidine Affinity Tag in Polyacrylamide Gels Using a Colorimetric Fluorescent Compound Fusion proteins containing a poly-histidine affinity tag were prepared and separated from *Escherichia coli* lysate proteins by SDS-polyacrylamide gel electrophoresis as described in Example 15. Following separation of the proteins on a SDS-polyacrylamide gel, the gels were fixed for 20 minutes in 100 ml of 50% ethanol/7% acetic acid and then fixed overnight in 100 ml of fresh fixative solution to ensure complete elimination of SDS. Gels were next washed 3 times for 20 minutes each in deionized water. The gels were then incubated in a staining solution containing 10 μM compound 9 or compound 10; 10 μM NiCl$_2$; 50 mM PIPES at pH 6.5 for 45-90 minutes in a total volume of 25 ml. Afterwards, the gels were washed 2 to 4 times for 20 minutes each in deionized water. The colorimetric signal from the poly-histidine affinity tag containing proteins was detected with a standard CCD camera-based imaging system with white light illumination and no filter according to standard Coomassie Blue or silver staining imaging methods.

Example 20

Detection of Glutathione S-Transferase (GST) with Texas Red® X-Glutathione Compound in Polyacrylamide Gels A purified sample of GST was separated by SDS-polyacrylamide gel electrophoresis utilizing 13% T, 2.6% C gels. % T is the total monomer concentration expressed in grams per 100 ml and % C is the percentage crosslinker. The 0.75 mm thick, 6×10 cm gels were subjected to electrophoresis using the Bio-Rad mini-Protean III system according to standard procedures.

Following separation of the protein on a SDS-polyacrylamide gel, the gel was fixed for 1 hour in 100 ml of 50% methanol/10% acetic acid and then fixed overnight in 100 ml of fresh fixative solution to ensure complete elimination of SDS. Gels were next washed 3 times for 20 minutes in deionized water. The gels were then incubated in a staining solution containing 5 µM Texas Red X-glutathione compound in 50 mM PIPES at pH 6.5 for 90 minutes in a total volume of 50 ml. Afterwards, the gels were washed 2 times for 20 minutes each in deionized water.

Figure 4:
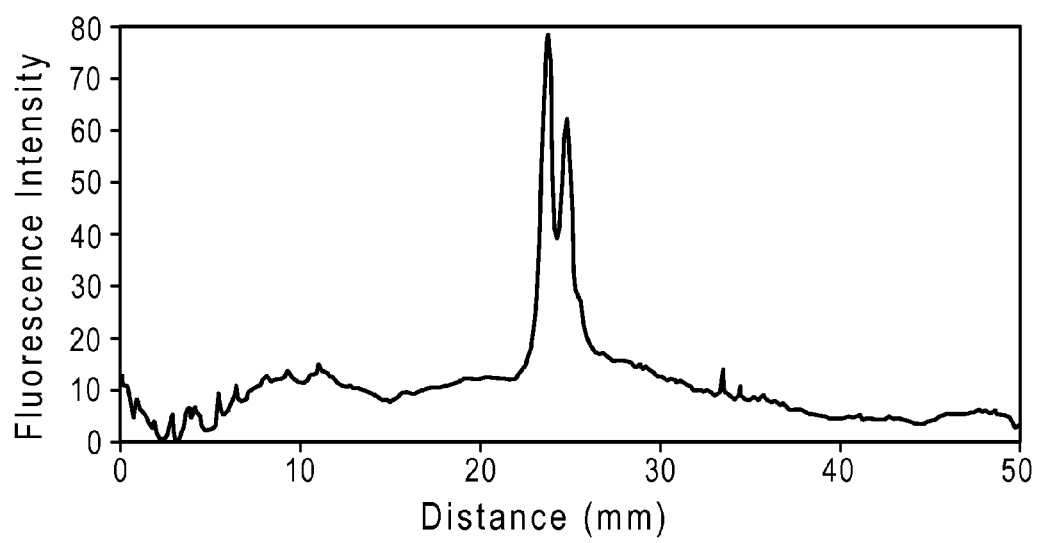
FIG. 4: Shows the detection of GST affinity tag using Texas Red X-glutathione fluorescent compound on a polyacrylamide gel. Purified glutathione S-transferase (1 µg) at 24 and 25 mm from the gel origin (2 peaks) stained with 5 µM Texas Red X-Glutathione in 50 mM PIPES pH 6.5. Imaged on the Fuji FLA3000 at 532 nm excitation, 580LP filter. See, Example 20.

The resulting red-fluorescent signal produced by Texas Red-glutathione was visualized using the 532 nm excitation line of the SHG laser on the Fuji FLA-3000G Fluorescence Image Analyzer (Fuji Photo, Tokyo, Japan) and 580 band pass emission filter. See, FIG. 4.

Example 21

Detection of Fusion Proteins Containing a Poly-Histidine Affinity Tag on a Membrane Blot

*Escherichia coli* lysates containing 6× histidine-tagged A subunit of ATPase and 6× histidine-tagged porin are fractionated by 13% T, 0.8% C SDS-polyacrylamide gel electrophoresis and electroblotted onto PVDF membrane. Blots are wetted with 100% methanol and then fixed with 50% methanol/7% acetic acid, briefly rinsed in deionized water and then stained for 15 minutes with either Pro-Q Sapphire 488 or Pro-Q Sapphire 532 gel stain solution. Blots are destained with two five-minute washes in 50 mM PIPES, pH 6.5, 20% acetonitrile to obtain fairly specific detection of the two his-tagged proteins. Blots are briefly washed in water and then dried before imaging. With both dyes, the two oligohistidine-tagged proteins are readily distinguished from other proteins in the lysate as brightly fluorescing bands. Limits of detection are approximately 20 ng.

Example 22

Detection of Fusion Proteins Containing a Poly-Histidine Affinity Tag on a Microarray Purified oligohistidine-tagged fusion proteins (the a subunit of *Escherichia coli* ATPase and porin), as well as control proteins (bovine serum albumin and ovalbumin) are arrayed from a source plate (384 well plate) concentration of 0.468 µg/ml-0.240 mg/ml in water, onto HydroGel coated slides (Perkin Elmer), using the BioChip Arrayer™ (Perkin Elmer). The BioChip Arrayer™ utilizes a PiezoTip™ Dispenser consisting of 4 glass capillaries. Proteins are dispensed from the PiezoTip™ by droplets 333 µl in volume to create array spots ~200 microns in diameter with a 500 micron horizontal and vertical pitch (pitch=center to center spacing of spots). Proteins are arrayed in duplicate in four rows, with 10 dilution points. The resulting concentration range of the array is 166.5 pg/spot-0.325 pg/spot. For detection of oligohistine-tagged proteins, slides are incubated for 45 minutes on a rotator in 50% ethanol/7% acetic acid and then fixed overnight in fresh fixative solution to ensure complete elimination of SDS. Microarrays are next washed 3 times for 20 minutes each in deionized water. The microarrays are then incubated in a staining solution containing 10 µM Compound 2 or Compound 15; 50 mM PIPES at pH 6.5 for 45-90 minutes. Afterwards, the microarrays are washed 2 to 4 times for 20 minutes each in deionized water. In order to ensure that the optimal signal was documented, gels are imaged after the second and fourth wash. Slides are then spun briefly in a microarray high-speed centrifuge affixed with a rotor with a slide holder (Telechem) at ~6000 rpm to remove excess liquid. After slides are dry, the arrays are imaged using the ScanArray® 5000 XL Microarray Analysis System (Packard Instrument Co., Meriden, Conn.) using the 488 nm laser and 522 nm emission filter. The oligohistine tagged proteins are detected as discrete fluorescent spots, while little or no signal generated on the control proteins. Detection sensitivity is less than 20 pg.

Example 23

Detection of Fusion Proteins Containing Poly-Arginine Affinity Tag in a Polyacrylamide Gel An *Escherichia coli* lysate containing an expressed oligo-arginine-tagged fusion protein (porin) is separated by SDS-polyacrylamide gel electrophoresis utilizing 13% T, 2.6% C gels. % T is the total monomer concentration expressed in grams per 100 ml and % C is the percentage crosslinker. The 0.75 mm thick, 6×10 cm gels are subjected to electrophoresis using the Bio-Rad mini-Protean III system according to standard procedures. Following separation of the proteins on a SDS-polyacrylamide gel, the gels are fixed for 20 minutes in 100 ml of 50% ethanol/7% acetic acid and then fixed overnight in 100 ml of fresh fixative solution to ensure complete elimination of SDS. Gels are next washed 3 times for 20 minutes each in deionized water. The gels are then incubated in a staining solution containing 10 µM compound 1 or 2 µM compound 2; 100 µM $NiCl_2$; 50 mM PIPES at pH 6.5 for 45-90 minutes in a total volume of 25 ml. Afterwards, the gels are washed 2 to 4 times for 20 minutes each in deionized water. In order to ensure that the optimal signal is documented, gels are imaged after the second and fourth wash.

The preceding examples can be repeated with similar success by substituting the specifically described fluorescent compound, affinity tag and staining conditions of the preceding examples with those generically and specifically described in the forgoing description. One skilled in the art can easily ascertain the essential characteristics of the present invention, and without departing from the spirit and scope thereof, can make various changes and modifications of the invention to adapt to various usages and conditions.

All publications, patents and patent applications mentioned in this specification are herein incorporated by reference to the same extent as if each individual publication, patent or patent application was specifically and individually indicated to be incorporated by reference.

What is claimed is:
1. A compound having the structure:
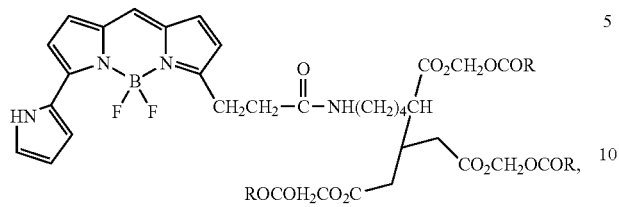
wherein R is an alkyl group.
* * * * *